United States Patent
Ahmed

(10) Patent No.: US 9,006,211 B2
(45) Date of Patent: *Apr. 14, 2015

(54) HYPERSULFATED DISACCHARIDE FORMULATIONS

(71) Applicant: OPKO Health, Inc., Miami, FL (US)

(72) Inventor: Tahir Ahmed, Coral Gables, FL (US)

(73) Assignee: OPKO Health, Inc., Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/011,807

(22) Filed: Aug. 28, 2013

(65) Prior Publication Data

US 2013/0345167 A1    Dec. 26, 2013

Related U.S. Application Data

(63) Continuation of application No. 12/953,831, filed on Nov. 24, 2010, now Pat. No. 8,546,351.

(60) Provisional application No. 61/266,361, filed on Dec. 3, 2009.

(51) Int. Cl.
*A61K 31/70* (2006.01)
*A61K 31/7016* (2006.01)

(52) U.S. Cl.
CPC ................................ *A61K 31/7016* (2013.01)

(58) Field of Classification Search
None
See application file for complete search history.

(56) References Cited

U.S. PATENT DOCUMENTS

| | | | | |
|---|---|---|---|---|
| 5,827,886 A | * | 10/1998 | Hersh | 514/562 |
| 7,056,898 B2 | * | 6/2006 | Ahmed et al. | 514/53 |
| 8,546,351 B2 | * | 10/2013 | Ahmed | 514/53 |
| 2003/0087875 A1 | * | 5/2003 | Ahmed et al. | 514/53 |

* cited by examiner

*Primary Examiner* — Traviss C McIntosh, III
(74) *Attorney, Agent, or Firm* — OPKO Health, Inc.; Monte R. Browder

(57) ABSTRACT

Hypersulfated disaccharides with utility in asthma or asthma related disorders are disclosed. The compounds are formulated with agents that enhance the oral delivery of the hypersulfated disaccharides. The delivery agents are selected from the group consisting of natural or synthetic polymers having ionic side chains as well as other compounds or types of compounds that improve the bioavailability of the disaccharides relative to delivery of the drug without such agents. The hypersulfated disaccharides are made from heparin or salts thereof.

20 Claims, 26 Drawing Sheets

* One Capsule (15 mg + Carbopol) Daily for 3 Days (PM)

* 2 Capsules ( 30 mg + Carbopol ) Daily for 3 Days (PM)

* 2 Capsules (30 mg + Carbopol) Daily for 3 Days (PM)

\* 3 Capsules ( 45 mg + Carbopol) Daily for 3 Days (PM)

* 3 Capsules Daily for 3 Days (PM)

* One Capsule (21 mg) Daily for 3 Days (PM)

* 1 Capsule (21 mg) Daily for 3 Days (PM)

* 1 Capsule (21 mg) Daily for 3 Days (PM) Without Carbopol

\* 1 Capsule ( 21 mg) Daily for 3 Days (PM) Without Carbopol

* 2 Capsules (21 mg) Daily x 3 Days (PM)/ Without Carbopol

* 2 Capsules (21 mg) Daily for 3 Days (PM) Without Carbopol

* 1 Capsule (15 mg) in Carbopol/Lactose for 3 Days (PM)

* 1Capsule (15mg) in Carbopol/Lactose for 3 Days (PM)

HYPERSULFATED DISACCHARIDE FORMULATIONS

CROSS REFERENCE TO RELATED APPLICATION

The present application claims priority to U.S. Provisional Patent Application Ser. No. 61/266,361, filed on Dec. 3, 2009 and Non Provisional Patent Application Ser. No. 12/953,831, filed on Nov. 24, 2010, all of which are incorporated by reference herein in their entirety.

FIELD OF THE INVENTION

The present invention relates to pharmaceutical formulations comprising a hypersulfated disaccharide compound of formula I as further described below and a delivery agent selected from a pharmaceutically acceptable vehicle (additive) that facilitates/enhances oral delivery of said compounds. The formulations are useful in the treatment of a variety of inflammatory disorders and diseases in animals and people, and, in particular, pulmonary disorders selected from asthma and other conditions or diseases associated with inflammation of the lungs and airway.

BACKGROUND OF THE INVENTION

U.S. Pat. No. 7,056,898 (the '898 patent) discloses and claims certain hypersulfated disaccharides and methods of using same to treat certain inflammatory disorders. This patent specifically describes the use of the claimed compounds to treat pulmonary inflammations including asthma and asthma-related pathologies, such as allergic reactions or an inflammatory disease or condition. The compounds disclosed therein are described as being capable of preventing, reversing and/or alleviating the symptoms of asthma and asthma-related pathologies, particularly the late phase response in asthma patients following antigen stimulation. The examples and figures shown therein specifically relate to intravenous and inhalation means of administration of the recited disaccharides. In the '898 patent there is a general disclosure of the oral administration of a hypersulfated disaccharide designated as 811-25-1 at a dose of 0.5 mgs/kg to sheep, but no specific data is shown. There is also no disclosure therein of any specific oral formulation nor any specific disclosure of any data related to administration of a specific oral formulation. There is a need for an improved pulmonary or anti-inflammatory medication that can be delivered in small dosages to patients in need of treatment thereof on a convenient basis and which does not have the side effects associated with, for example, chronic administration of steroids or leukotriene receptor antagonists such as montelukast sodium.

The inventor has met this unmet need and has surprisingly found that certain formulations comprising the hypersulfated disaccharides recited herein and a delivery agent selected from the group consisting of a pharmaceutically acceptable natural or synthetic polymer as well as other vehicles that heretofore have been utilized to improve delivery of large compounds (e.g., those compounds having molecular weights of greater than 4,500 daltons as average molecular weight) have enhanced absorption/bioavailability/efficacy relative to the same compounds delivered without the claimed additives. While the literature has disclosed that certain carbomers enhance the intestinal absorption of Low Molecular Weight Heparins (LMWH) having, molecular weights of approximately 4500 daltons, there has been no teaching or suggestion of the use of such materials to enhance the absorption of low molecular weight disaccharides. In fact, as reported in Thanou et al., Pharmaceutical Research, 18 (11) 2001, such carbomers were added because of the large size of the LMWHs which, it was thought, would have difficulty permeating across the intestinal epithelium via transcellular or paracellular routes (via passage through the tight junction) albeit with less difficulty than fractions having a molecular weight of 12,000 daltons. The same would not apply to low molecular disaccharides which are, when compared to LMWHs, small molecules which can more readily permeate across the intestinal epithelium. The present inventors have unexpectedly found that low molecular weight disaccharides, in particular, low molecular weight hypersulfated disaccharides (e.g., of about 1,000 daltons), have surprisingly better efficacy when combined with a polymeric material having at least one of the chemical and/or physical properties of, for example, Carbopol 934 P and/or other carbomers. Such polymers have ionic groups such as a carboxylic acid side chain and/or hydrophilic moieties which facilitate the delivery of the hypersulfated disaccharides of the invention.

SUMMARY OF THE INVENTION

The present invention relates to pharmaceutical formulations comprising a compound of formula I and pharmaceutically acceptable salts thereof and a delivery agent selected from the group consisting of a pharmaceutically acceptable synthetic polymer or natural polymer, an oligomer or other agent that facilitates the delivery or administration of a compound of formula into the bloodstream of an animal. The compound in the formulation is a compound of formula I or a pharmaceutically acceptable salt thereof,

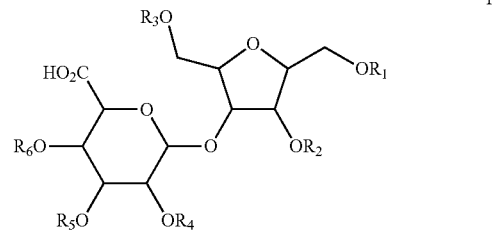

wherein $R_1$, $R_2$, $R_3$, $R_4$, $R_5$ and $R_6$ are independently selected from the group consisting of H, $SO_3H$ or $PO_3H$ and provided that at least two of $R_1$-$R_6$ is selected from $SO_3H$ or $PO_3H$. The present invention also relates to formulations having a compound of formula I wherein at least three of $R_1$-$R_6$ are selected from $SO_3H$ or $PO_3H$. The present invention further relates to formulations having compounds of formula I wherein at least four of $R_1$-$R_6$ are selected from $SO_3H$ or $PO_3H$. The present invention further relates to formulations having compounds of formula I wherein at least five of $R_1$-$R_6$ are selected from $SO_3H$ or $PO_3H$. The present invention preferably relates to a compound of formula I and pharmaceutically acceptable salts thereof wherein $R_1$-$R_6$ are selected from $SO_3H$. The present invention also relates to formulations having a compound of formula I wherein $R_1$-$R_6$ are independently selected from $SO_3H$ or $PO_3H$. The invention further includes pro-drugs, derivatives, active metabolites, partially ionized and fully ionized derivatives of the compounds of formula I and stereoisomers thereof. The monomers which make up the disaccharides of the invention may be D or L isomers and the hydroxyl moieties or sulfated or phosphated versions thereof around the carbocyclic ring (or acyclic versions or intermediates thereof) may have the alpha or beta designation at any particular stereocenter. The linking oxygen atom between the monosaccharide moieties may also be alpha or beta. The molecular weight of the compounds of the invention is typically less than 1,000 daltons.

The present invention also relates to a pharmaceutical formulation comprising
- (i) a compound of formula I and pharmaceutically acceptable salts thereof

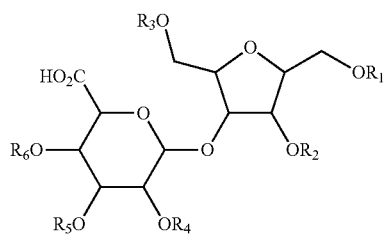

I wherein $R_1$, $R_2$, $R_4$, $R_5$ and $R_6$ are independently selected from H, $SO_3H$ or $PO_3H$ and $R_3$ is independently selected from $SO_3H$ or $PO_3H$ and
- (ii) an additive selected from the group consisting of a pharmaceutically acceptable natural or synthetic polymer.

The present invention also relates to a pharmaceutical formulation comprising
- (i) a compound of formula I and pharmaceutically acceptable salts thereof

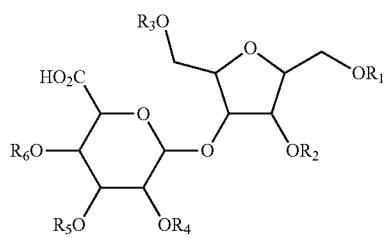

I wherein $R_1$, $R_2$, $R_5$ and $R_6$ are independently selected from H, $SO_3H$ or $PO_3H$ and $R_3$ and $R_4$ are independently selected from $SO_3H$ or $PO_3H$ and
- (ii) an additive selected from the group consisting of a pharmaceutically acceptable natural or synthetic polymer.

The invention relates to a pharmaceutical formulation comprising
- (i) a compound of formula I and pharmaceutically acceptable salts thereof

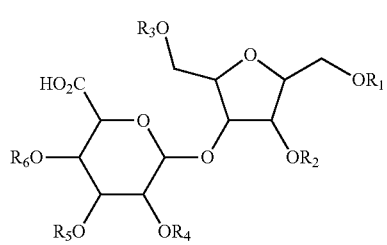

I wherein $R_1$, $R_2$ and $R_6$ are independently selected from H, $SO_3H$ or $PO_3H$ and $R_3$, $R_4$ and $R_5$ are independently selected from $SO_3H$ or $PO_3H$ and
- (ii) an additive selected from the group consisting of a pharmaceutically acceptable natural or synthetic polymer.

In another embodiment, the present invention relates to a pharmaceutical formulation comprising
- (i) a compound of formula II

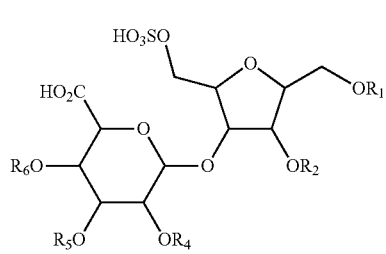

II and pharmaceutically acceptable salts thereof wherein $R_1$, $R_2$, $R_4$, $R_5$ and $R_6$ are independently selected from the group consisting of H, $SO_3H$ or $PO_3H$ and
- (ii) an additive selected from the group consisting of a pharmaceutically acceptable natural or synthetic polymer.

In a preferred embodiment, the invention relates to a pharmaceutical formulation comprising
- (i) a compound of formula II and pharmaceutically acceptable salts thereof wherein $R_1$ is $SO_3H$ and $R_2$, $R_4$, $R_5$ and $R_6$ are independently selected from H, $SO_3H$ or $PO_3H$ and
- (ii) an additive selected from the group consisting of a pharmaceutically acceptable natural or synthetic polymer.

In an additional preferred embodiment, the invention relates to a pharmaceutical formulation comprising
- (i) a compound of formula II and pharmaceutically acceptable salts thereof wherein R1 is SO3H, R2 is H and R4, R5 and R6 are independently selected from SO3H or PO3H and
- (ii) an additive selected from the group consisting of a pharmaceutically acceptable natural or synthetic polymer. The most preferred embodiment relates to a pharmaceutical formulation containing a compound of formula I and pharmaceutically acceptable salts thereof wherein R1-R6 are selected from SO3H.

The present invention also relates to oral dosage forms comprising a compound of formula I or II wherein $R_1$-$R_6$ have any of the designations shown above and their pharmaceutically acceptable salts and an additive selected from the group consisting of a pharmaceutically acceptable natural or synthetic polymer.

The present invention also encompasses a method of treating an inflammatory condition in an organism in need of treatment thereof comprising administering a pharmaceutically effective amount of a formulation comprising a compound of formula I

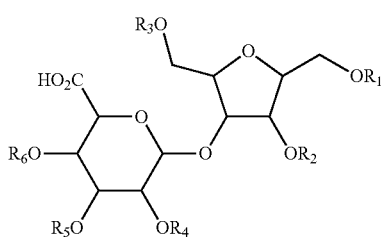

I and pharmaceutically acceptable salts thereof wherein $R_1$-$R_6$ are independently selected from $SO_3H$, $PO_3H$ or H and provided that at least two of $R_1$-$R_6$ is $SO_3H$ or $PO_3H$ and a delivery agent selected from the group consisting of a pharmaceutically acceptable natural or synthetic polymer, oligomer or agent that facilitates the delivery of a compound of formula I into the bloodstream and/or to a target site and which prevents or mitigates an inflammatory response to an antigen.

BRIEF DESCRIPTION OF THE DRAWINGS

The invention will be described in the following drawings.

(open circles). Data shown are antigen-induced mean plus or minus SE % change in $SR_L$ in four sheep (n=4) exposed to antigen first with no drug and then again several weeks later with antigen after being pretreated for three days (×3 days) before antigen exposure with a single liquid oral dose of 2 mg/kg MD1599-8 per day administered in the evening (P.M. dose). Antigen challenge was 15 hours following the last 2 mg/kg drug administration.

Figure 5A:
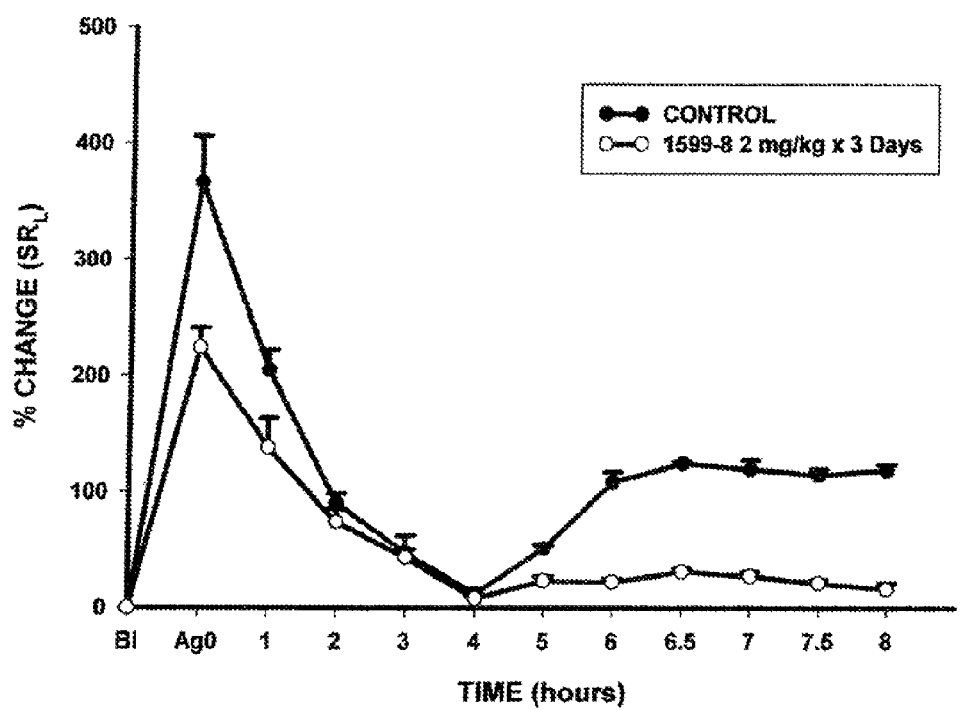
FIG. 5A shows a graph comparing the percentage change in specific pulmonary airflow resistance (measured as cm $H_2O/L/sec$) (i.e., the $SR_L$) following the indicated time after antigen administration (time=0) of sheep's responses (n=4) to exposure to antigen only (closed circles) (control) and antigen plus a liquid oral dosage of 2 mg/kg of the hexasulfated disaccharide designated as MD1599-8 (compound 14a) or the fully ionized sodium salt form of compound 14 in Table 1
Figure 5B:
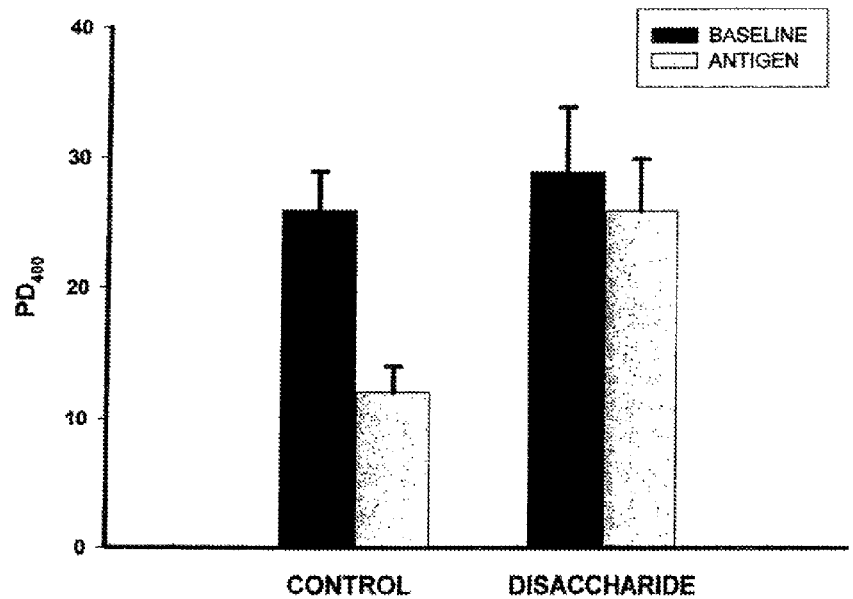

FIG. 5B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=4) exposed to antigen first with no drug and then again with antigen several weeks later following pretreatment for three days before exposure with an oral dose of MD1599-8 (compound 14a) (2 mg/kg) administered in the evening on three successive days (2 mg/kg/day). Antigen exposure occurred 15 hours after the last 2 mg/kg treatment.

Figure 6A:
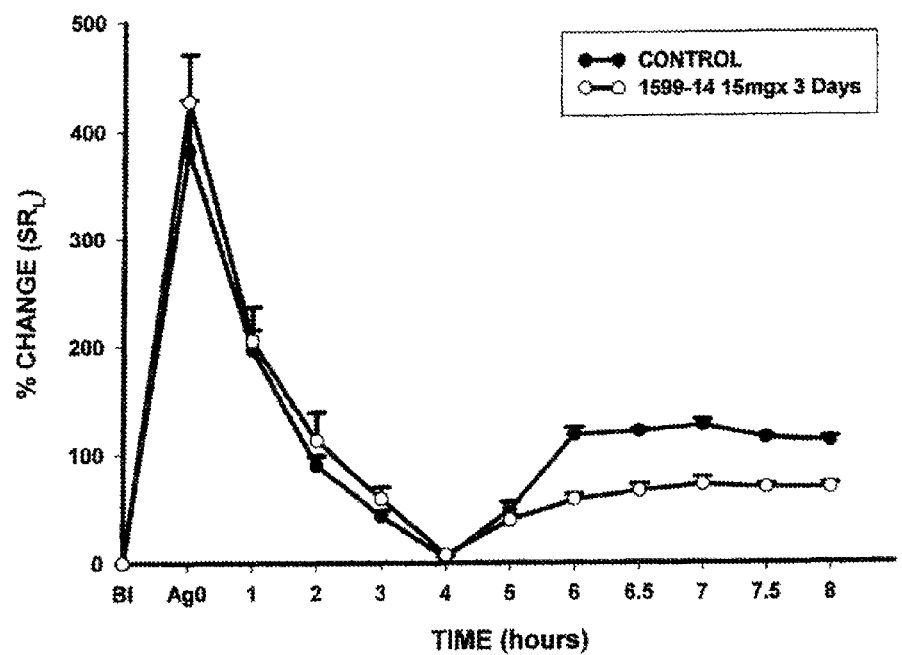

FIG. 6A shows a graph comparing the percentage change in specific pulmonary airflow resistance (measured as cm $H_2O$/L/sec) (i.e., the $SR_L$) following the indicated time after antigen administration (time=0) of sheep's responses (n=5) to exposure to antigen only (closed circles) (control) and antigen plus one daily oral capsule dosage form having 15 mg of the hexasulfated disaccharide (the fully ionized sodium salt form of compound 14 as shown in Table 1 (or compound 14a)) and 15 mg of an additive selected from Carbopol 934 P NF (open circles) and lactose filler with the formulation designated as 1599-14. Data are shown as antigen-induced mean plus or minus SE % change in $SR_L$ in five sheep (n=5) exposed to antigen first with no drug and then again several weeks later with antigen after being pretreated for three days (×3 days) before antigen exposure with a single daily dosage of 15 mgs of compound 14 sodium salt (aka compound 14a)/ 15 mgs Carbopol 934P NF administered in the evening (P.M. dose) in capsule form. Antigen challenge occurred 15 hours following the last 15 mg compound 14a treatment.

Figure 6B:
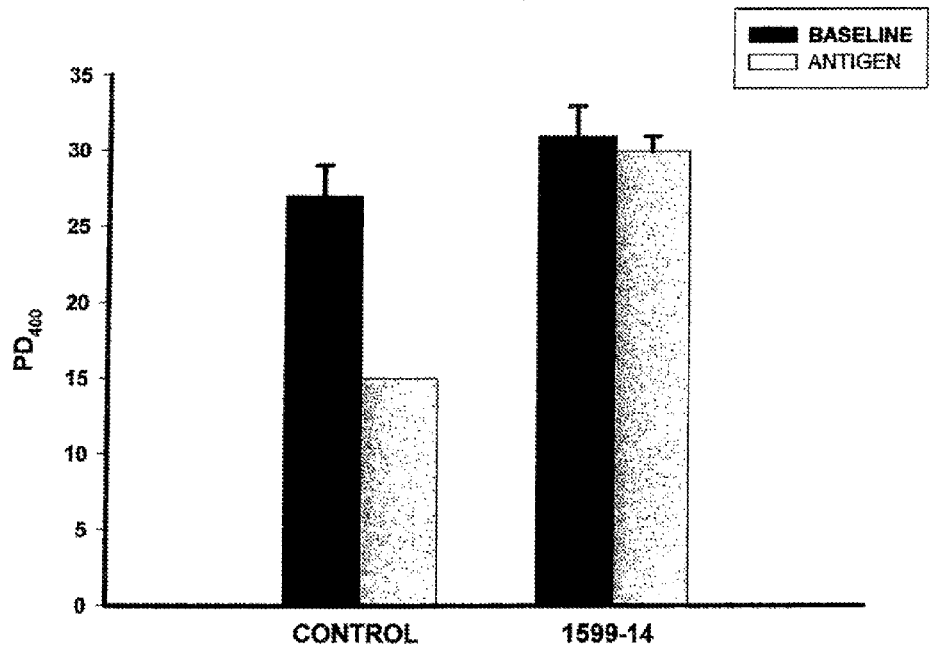

FIG. 6B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pretreatment for 3 days before exposure with a daily oral dose of a formulation comprising compound 14 sodium salt (compound 14a) (15 mgs) and Carbopol 934P (15 mgs) administered in the evening in capsule form (formulation 1599-14). Antigen challenge occurred 15 hours following the last 15 mg compound 14a treatment.

Figure 7A:
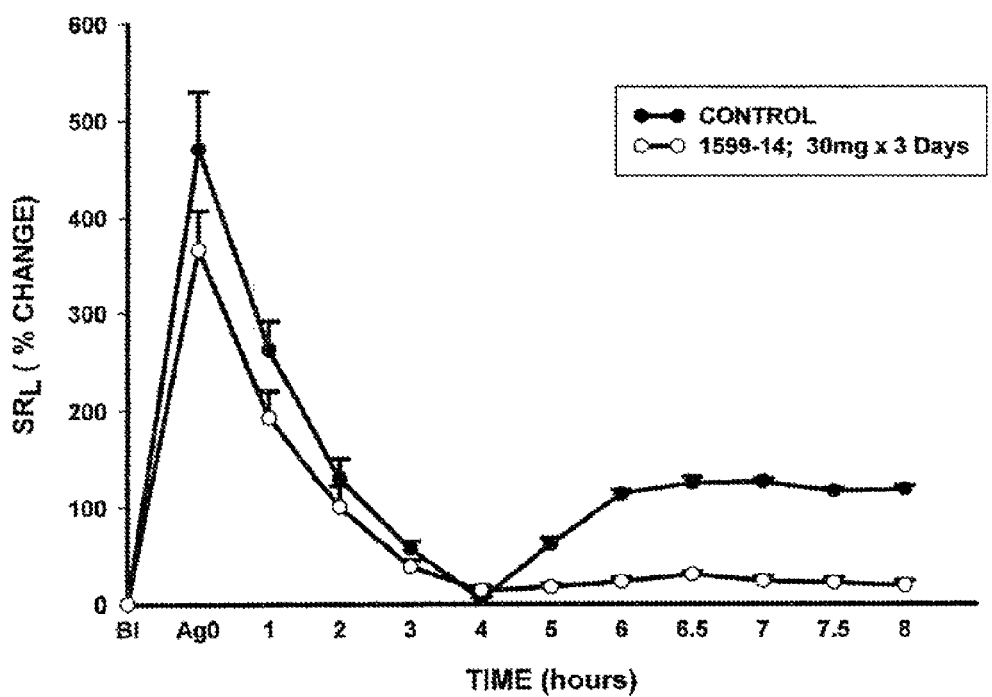

FIG. 7A shows a graph comparing the percentage change in specific pulmonary airflow resistance (measured as cm $H_2O$/L/sec) (i.e., the $SR_L$) following the indicated time after antigen administration (time=0) of sheep's responses (n=5) to exposure to antigen only (closed circles) (control) and antigen plus two daily oral capsule dosage forms having 15 mg of the hexasulfated disaccharide (the fully ionized sodium salt form of compound 14 as shown in Table 1 aka compound 14a) and 15 mg of an additive selected from Carbopol 934P (open circles) with the formulation designated as 1599-14. Data are shown as antigen-induced mean plus or minus SE % change in $SR_L$ in five sheep (n=5) exposed to antigen first with no drug and then again several weeks later with antigen after being pretreated for three days (×3 days) before antigen exposure with a daily dosage of 30 mgs of compound 14 sodium salt (aka 14a)/30 mgs Carbopol 934P administered in the evening (P.M. dose) in capsule form (2 capsules per day administered at the same time or immediately following one another). Antigen exposure occurred 15 hours after the last 30 mg dosing.

Figure 7B:
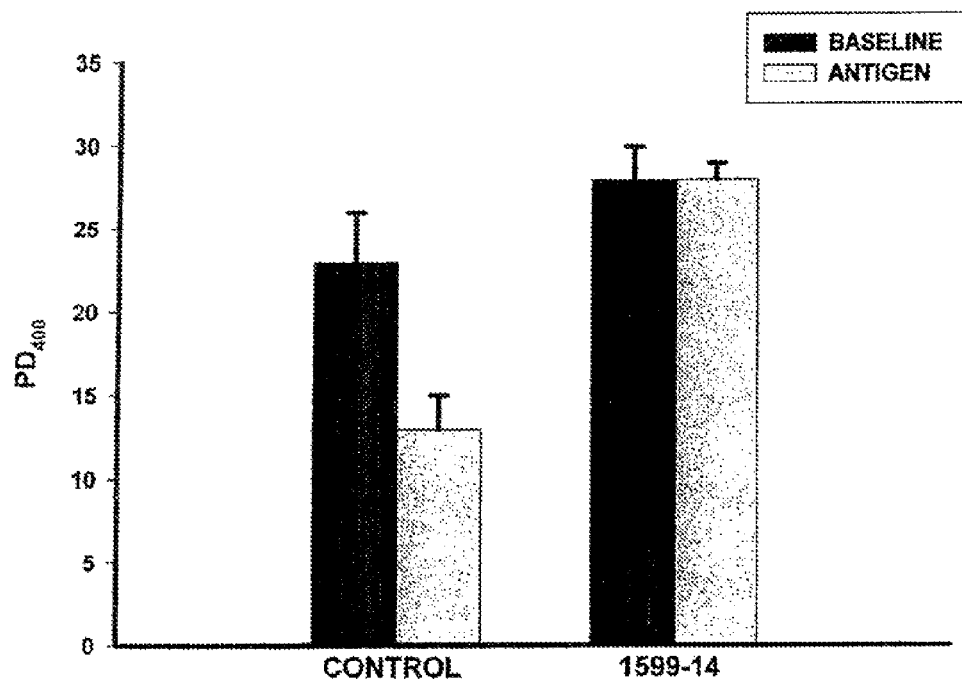

FIG. 7B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pretreatment for 3 days before exposure with a daily oral dose of a formulation comprising compound 14 sodium salt (compound 14a) (15 mgs) and Carbopol 934 P (15 mgs) administered in the evening in capsule form (formulation 1599-14) as two capsules/day to provide a total of 30 mgs/day of active ingredient each day for the three day period. Antigen exposure occurred 15 hours after the last 30 mg treatment.

Figure 8A:
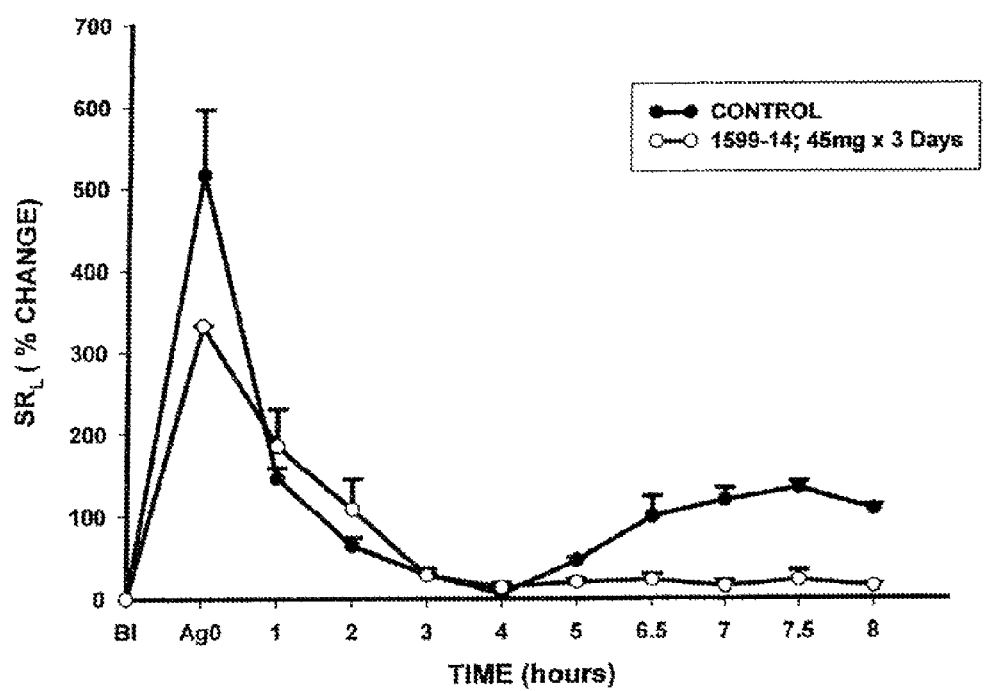

FIG. 8A shows a graph comparing the percentage change in specific pulmonary airflow resistance (measured as cm $H_2O$/L/sec) (i.e., the $SR_L$) following the indicated time after antigen administration (time=0) of sheep's responses (n=2) to exposure to antigen only (closed circles) (control) and antigen plus three daily oral dosage capsule forms each having 15 mg of the hexasulfated disaccharide (the fully ionized sodium salt form of compound 14 as shown in Table 1—aka 14a) and 15 mg of an additive selected from Carbopol 934 P (open circles) with the formulation designated as 1599-14. Data are shown as antigen-induced mean plus or minus SE % change in $SR_L$ in two sheep (n=2) exposed to antigen first with no drug and then again several weeks later with antigen after being pretreated for three days (×3 days) before antigen exposure with a daily dosage of 45 mgs of compound 14 sodium salt (aka 14a)/45 mgs Carbopol 934P administered in the evening (P.M. dose) in capsule form (3 capsules per day). Antigen exposure occurred 15 hours following the last 45 mg evening dose.

Figure 8B:
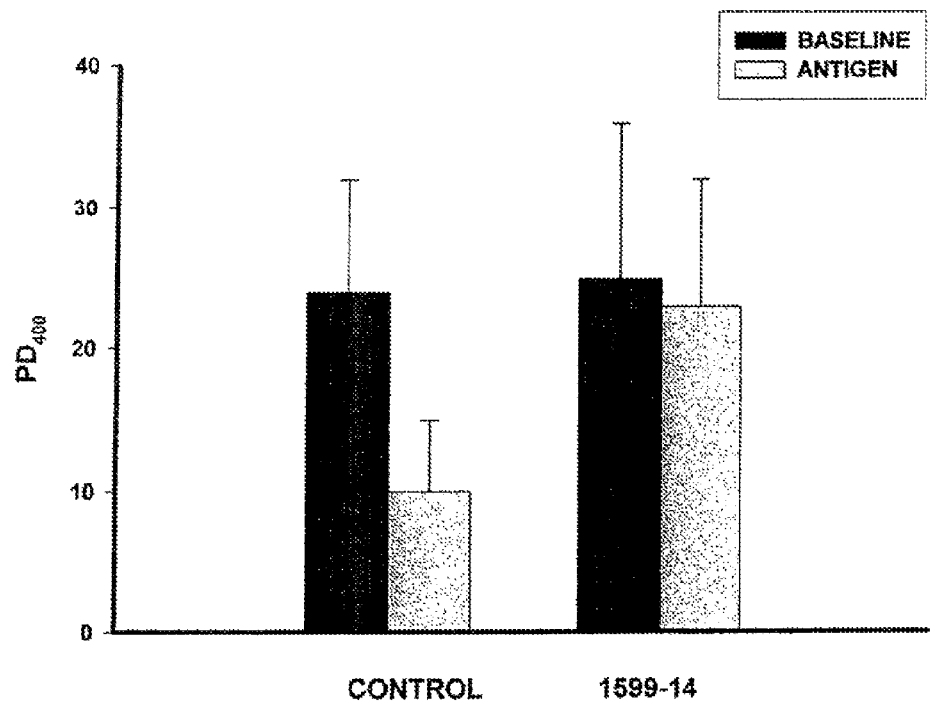

FIG. 8B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=2) exposed to antigen first with no drug and then again with antigen several weeks later following pretreatment 3 days before exposure with a daily oral dose of a formulation comprising compound 14 sodium salt (14a) (15 mgs) and Carbopol 934 P (15 mgs) administered in the evening in capsule form (formulation 1599-14) as three capsules/day to provide a total of 45 mgs/ day of active ingredient and 45 mgs Carbopol 934 P each day for the three day period. Antigen exposure occurred 15 hours following the last evening 45 mg dose of compound 14a.

Figure 9A:
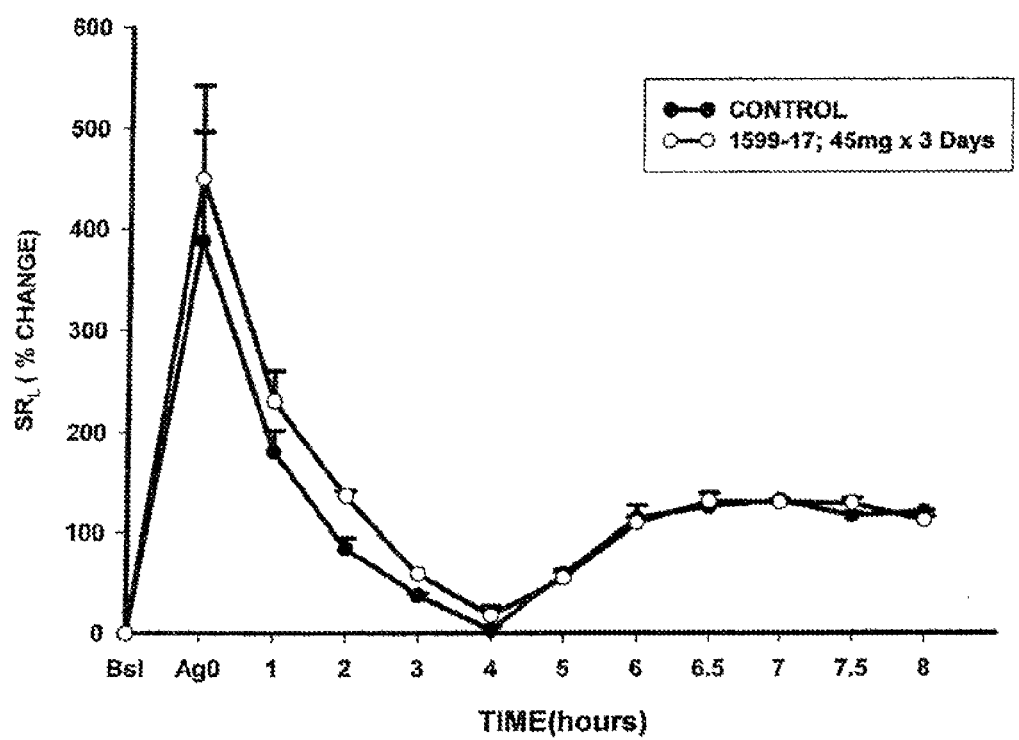

FIG. 9A shows a graph comparing the percentage change in specific pulmonary airflow resistance (measured as cm $H_2O$/L/sec) (i.e., the $SR_L$) following the indicated time after antigen administration (time=0) of sheep's responses (n=2) to exposure to antigen only (closed circles) (control) and antigen plus three daily oral capsule dosage forms, each having 15 mgs Carbopol 934P in lactose filler (open circles) with the formulation designated as 1599-17. Data are shown as antigen-induced mean plus or minus SE % change in $SR_L$ in two sheep (n=2) exposed to antigen first with no additive and then again several weeks later with antigen after being pretreated for three days (×3 days) before antigen exposure with a total daily dosage of 45 mgs Carbopol additive administered in the evening (P.M. dose) in capsule form (3 capsule per day×3 days).

Figure 9B:
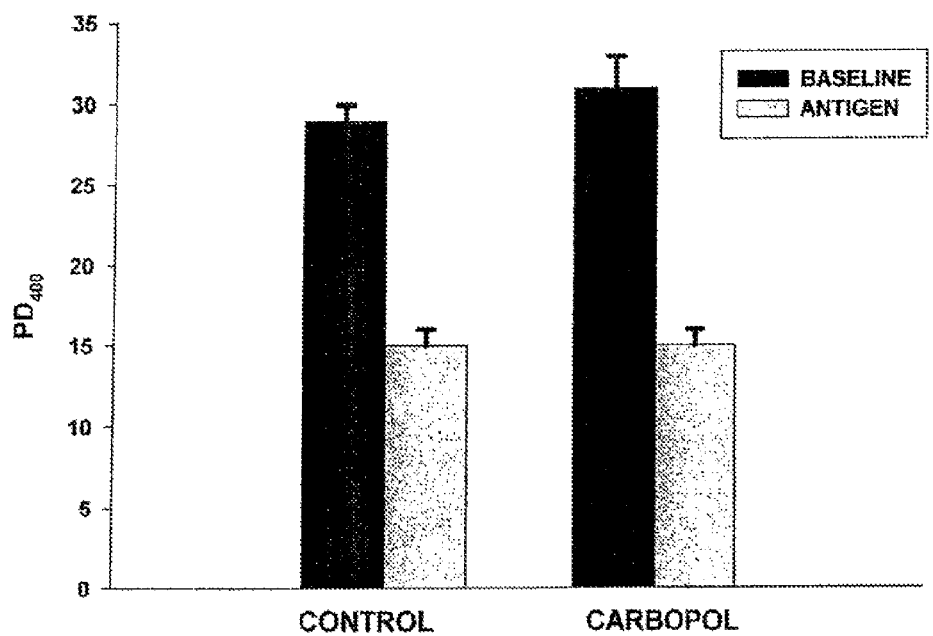

FIG. 9B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=2) exposed to antigen first with no additive and then again with antigen several days later following pretreatment for 3 days before exposure with a daily oral dose of a formulation comprising Carbopol 934 P (15 mgs per capsule in lactose) administered in the evening in capsule form (formulation 1599-17) as three capsules/day for the three day period for a total dosage of Carbopol of 45 mgs/day.

Figure 10A:
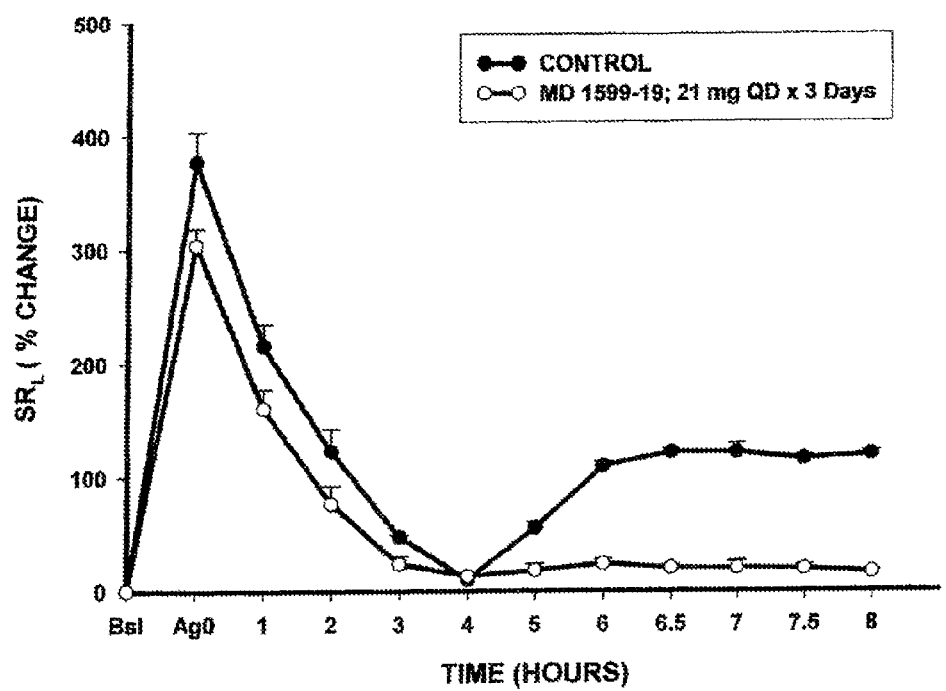

FIG. 10A shows a graph comparing the percentage change in specific pulmonary airflow resistance (measured as cm $H_2O/L/sec$) (i.e., the $SR_L$) following the indicated time after antigen administration (time=0) of sheep's responses (n=5) to exposure to antigen only (closed circles) (control) and antigen plus a single daily oral capsule dosage form having 21 mgs of the hexasulfated disaccharide (the fully ionized sodium salt form of compound 14 as shown in Table 1 aka 14a) and 21 mgs of an additive selected from Carbopol 934 P (open circles) with the formulation designated as 1599-19. Data are shown as antigen-induced mean plus or minus SE % change in $SR_L$ in five sheep (n=5) exposed to antigen first with no drug and then again several weeks later with antigen after being pretreated for three days (×3 days) before antigen exposure with a daily dosage of 21 mgs of compound 14 sodium salt (14a)/21 mgs Carbopol 934 P administered in the evening (P.M. dose) in capsule form (1 capsule per day). Antigen exposure occurred 15 hours after the last evening 21 mg dose.

Figure 10B:
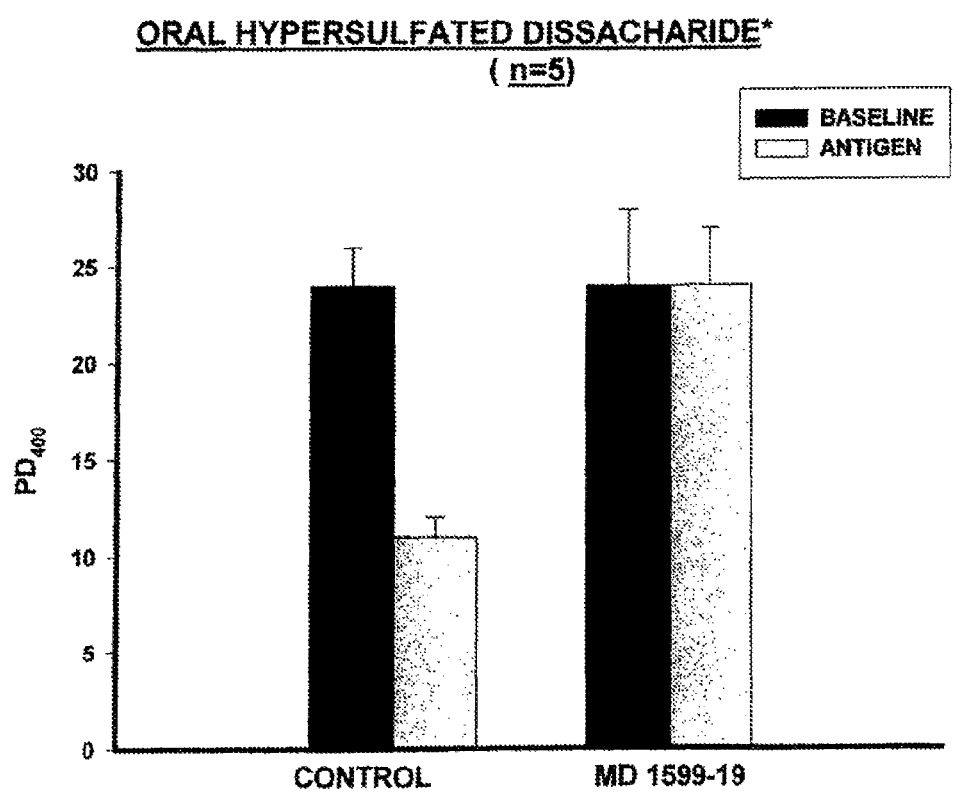

FIG. 10B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pretreatment for 3 days before exposure with a daily oral dose of a formulation comprising compound 14 sodium salt (14a) (21 mgs) and Carbopol 934 P (21 mgs) administered in the evening in capsule form (formulation 1599-19) as one capsule/day for the three day period. Antigen exposure occurred 15 hours after the last evening 21 mg dose of compound 14a.

Figure 11A:
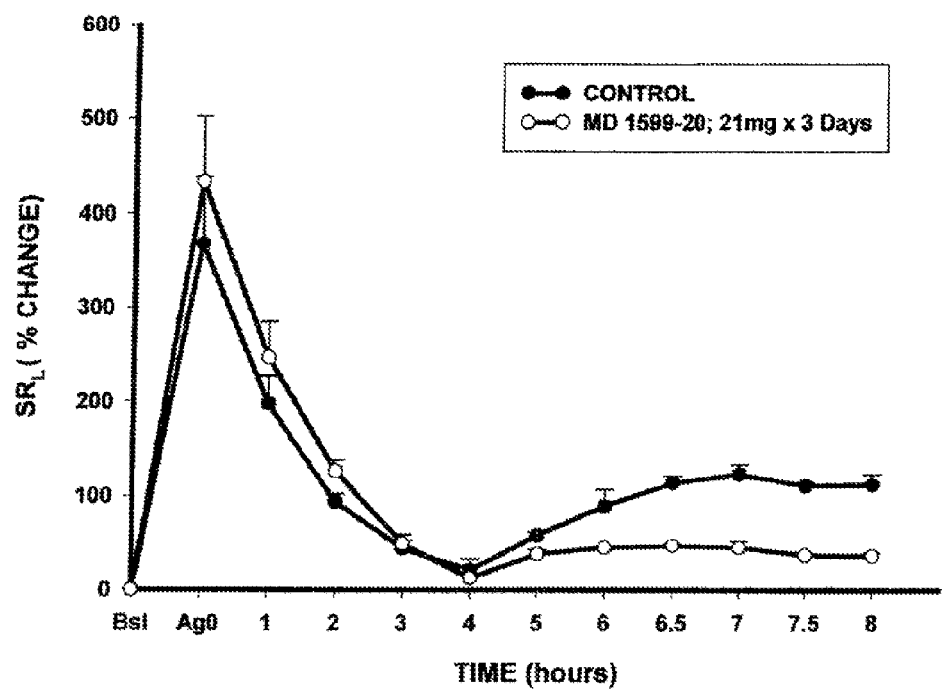

FIG. 11A shows a graph comparing the percentage change in specific pulmonary airflow resistance (measured as cm $H_2O/L/sec$) (i.e., the $SR_L$) following the indicated time after antigen administration (time=0) of sheep's responses (n=3) to exposure to antigen only (closed circles) (control) and antigen plus a single daily oral capsule dosage form having 21 mgs of the hexasulfated disaccharide (the fully ionized sodium salt form of compound 14 as shown in Table 1 (aka 14a) (open circles) with the formulation designated as 1599-20. Data are shown as antigen-induced mean plus or minus SE % change in $SR_L$ in five sheep (n=3) exposed to antigen first with no drug and then again several weeks later with antigen after being pretreated for three days (×3 days) before antigen exposure with a daily dosage of 21 mgs of compound 14 sodium salt (14a) administered in the evening (P.M. dose) in capsule form (1 capsule per day). Antigen exposure occurred 15 hours after the last evening 21 mg dose.

Figure 11B:
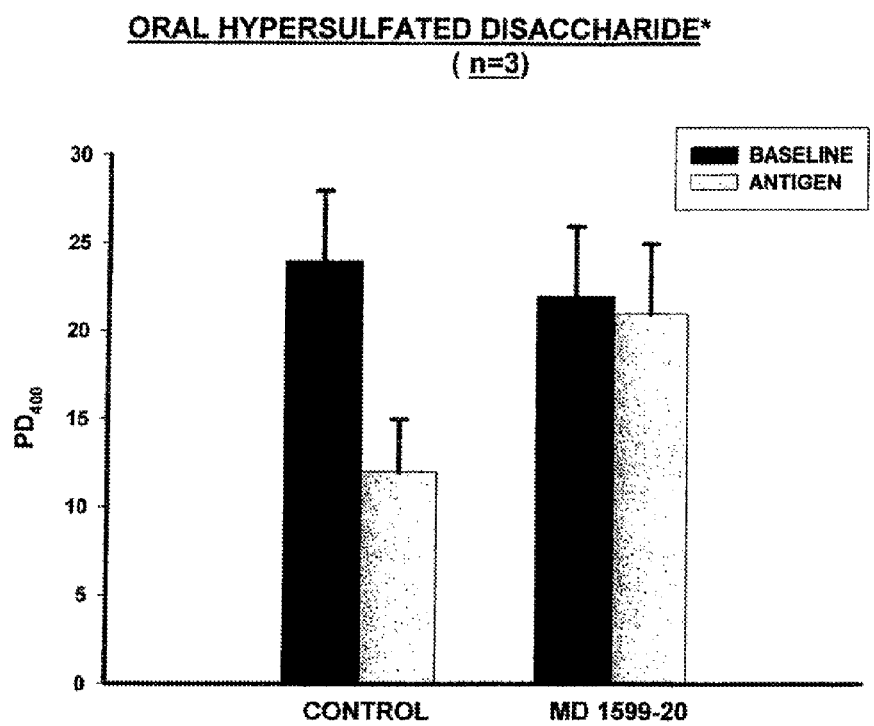

FIG. 11B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=3) exposed to antigen first with no drug and then again with antigen several weeks later following pretreatment for 3 days before exposure with a daily oral dose of a formulation comprising compound 14 sodium salt (14a) (21 mgs) administered in the evening in capsule form (formulation 1599-20) as one capsule/day for the three day period. Antigen exposure occurred 15 hours after the last evening 21 mg dose of compound 14a.

Figure 12A:
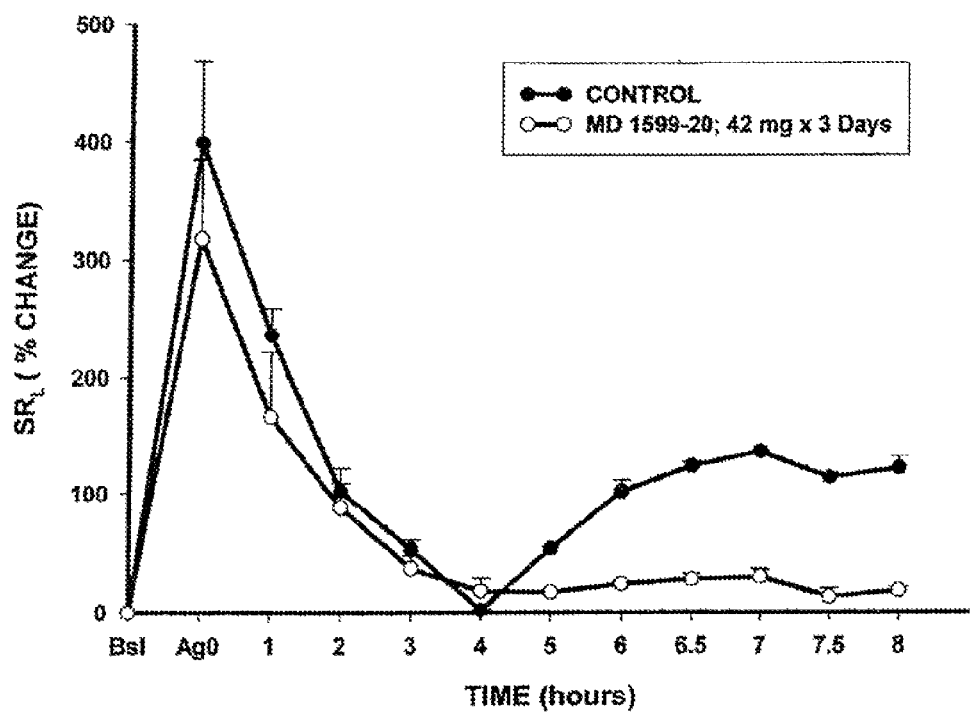

FIG. 12A shows a graph comparing the percentage change in specific pulmonary airflow resistance (measured as cm $H_2O/L/sec$) (i.e., the $SR_L$) following the indicated time after antigen administration (time=0) of sheep's responses (n=2) to exposure to antigen only (closed circles) (control) and antigen plus two daily oral capsule dosage form having 21 mgs of the hexasulfated disaccharide (42 mgs total active) (the fully ionized sodium salt form of compound 14 as shown in Table 1 aka 14a) (open circles) with the formulation designated as 1599-20 42 mgs. Data are shown as antigen-induced mean plus or minus SE % change in $SR_L$ in five sheep (n=2) exposed to antigen first with no drug and then again several weeks later with antigen after being pretreated for three days (×3 days) before antigen exposure with a daily dosage of 42 mgs of compound 14 sodium salt (14a) administered in the evening (P.M. dose) in capsule form (2 capsules per day taken at the same time). Antigen exposure occurred 15 hours after the last evening 42 mg dose.

Figure 12B:
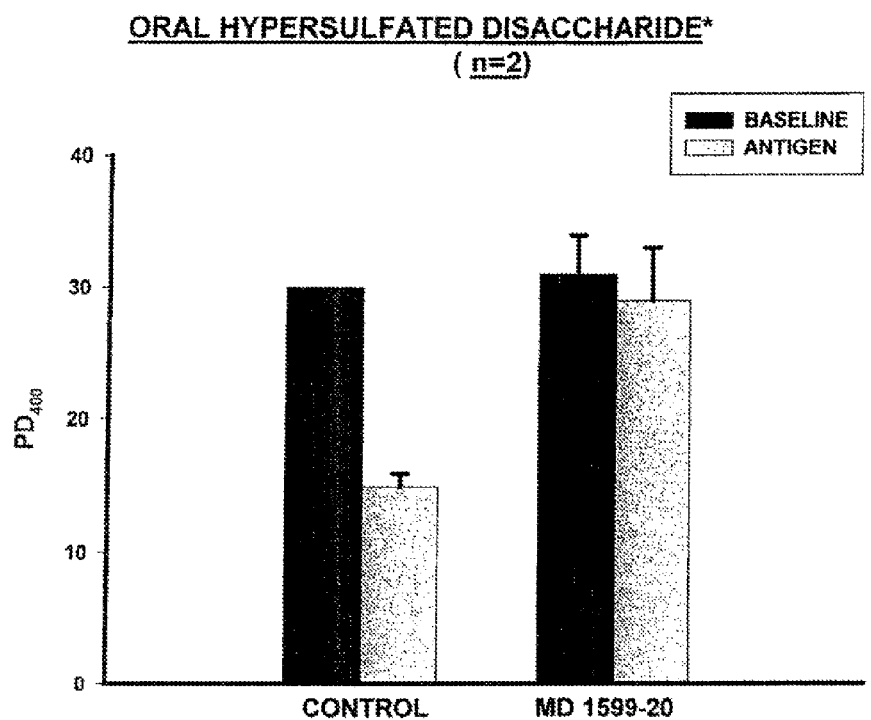

FIG. 12B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=2) exposed to antigen first with no drug and then again with antigen several weeks later following pretreatment for 3 days before exposure with a daily oral dose of a formulation comprising compound 14 sodium salt (14a) (42 mgs) administered in the evening in capsule form (formulation 1599-20 42 mgs) as two capsules/day taken at the same time for the three day period. Antigen exposure occurred 15 hours after the last evening 42 mg dose of compound 14a.

Figure 13A:
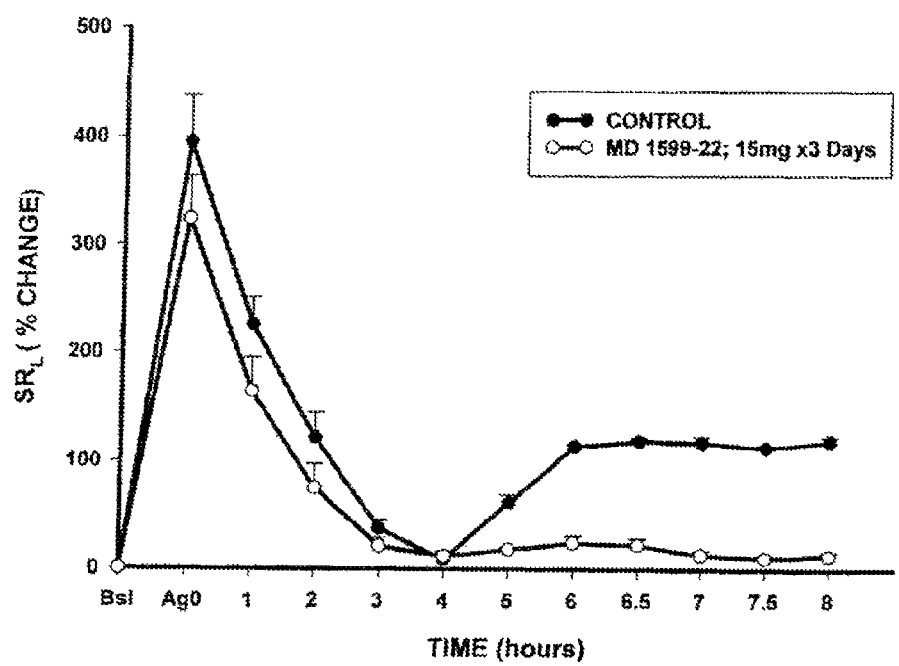

FIG. 13A shows a graph comparing the percentage change in specific pulmonary airflow resistance (measured as cm $H_2O/L/sec$) (i.e., the $SR_L$) following the indicated time after antigen administration (time=0) of sheep's responses (n=5) to exposure to antigen only (closed circles) (control) and antigen plus a single daily oral capsule dosage form having 15 mgs of the hexasulfated disaccharide compound 14a (the fully ionized sodium salt form of compound 14 as shown in Table 1) and 30 mgs of an additive selected from Carbopol 934 P (closed triangles) with the formulation designated as 1599-22. Data are shown as antigen-induced mean plus or minus SE % change in $SR_L$ in five sheep (n=5) exposed to antigen first with no drug and then again several weeks later with antigen after being pretreated for three days (×3 days) before antigen exposure with a daily dosage of 15 mgs of compound 14 sodium salt (compound 14a)/30 mgs Carbopol 934 P administered in the evening (P.M. dose) in capsule form (1 capsule per day). Antigen exposure occurred 15 hours following the last evening 15 mg dosage form.

Figure 13B:
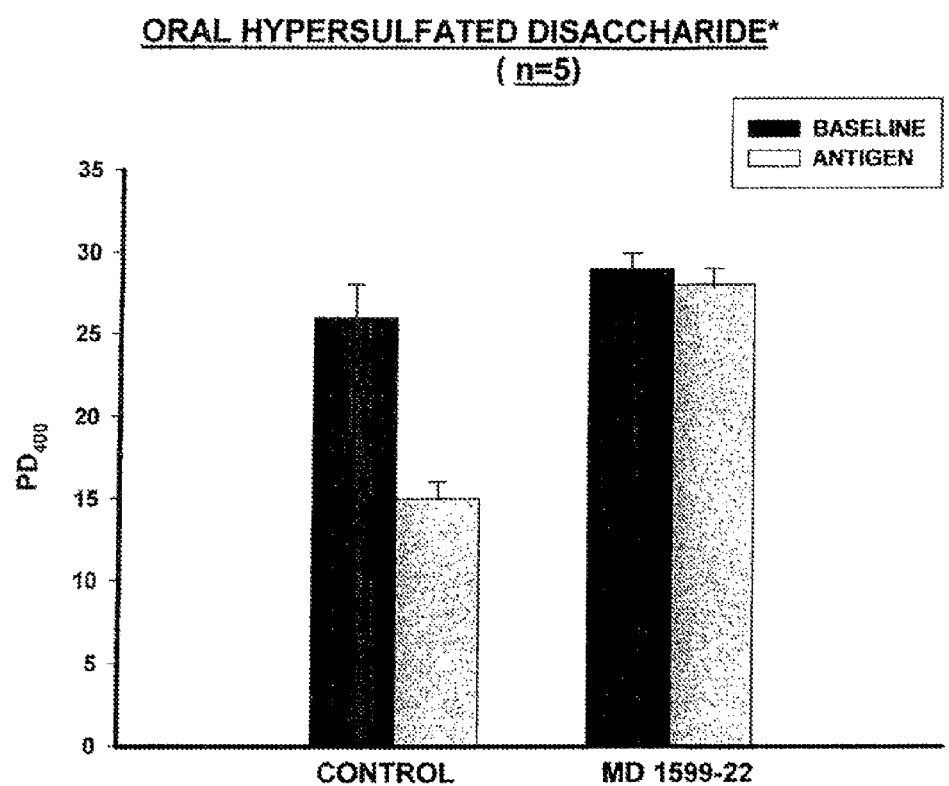

FIG. 13B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several days later following pretreatment for 3 days before exposure of antigen with a daily oral dose of a formulation comprising compound 14 sodium salt (15 mgs compound 14a) and Carbopol (30 mgs) administered in the evening in capsule form (formulation 1599-22) as one capsule/day for the three day period. Antigen exposure occurred 15 hours following the last 15 mg evening dosage form. The capsules utilized in the above Figures were enteric coated.

DETAILED DESCRIPTION

The present invention relates to pharmaceutical formulations and uses thereof wherein the formulation comprises a compound of formula I and pharmaceutically acceptable salts thereof

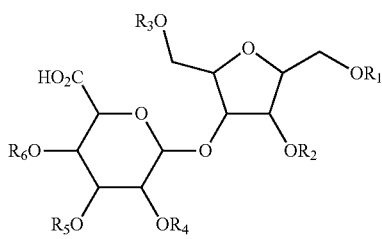

I wherein $R_1$, $R_2$, $R_3$, $R_4$, $R_5$ and $R_6$ are independently selected from the group consisting of H, $SO_3H$ or $PO_3H$ and provided that at least two of $R_1$-$R_6$ is selected from $SO_3H$ or $PO_3H$ and a delivery agent selected from the group consisting of a pharmaceutically acceptable natural or synthetic polymer, oligomer or agent that facilitates the delivery of compound I into the bloodstream. The term "pharmaceutically acceptable natural or synthetic polymer" generally means a pharmaceutically acceptable naturally derived or synthetic polymer having repeating units of a monomer or monomeric unit having a carbon chain or backbone (saturated or unsaturated or having both unsaturated and saturated monomers) with side chain substituents on the monomeric unit(s). Such polymers can be homopolymers or copolymers of repeating monomeric units wherein adjacent monomers can be the same or different. The side chain substituents include carboxylic acid groups or other polar groups selected from hydroxyl or amino groups and which can be further substituted with, for example, sulfate or phosphate groups. The polymers can be crosslinked. The preferred monomer is an acrylic acid residue and which forms carbomers. The molecular weight of such polymers can be around 500,000 to about 4 Billion. The molecular weight between crosslinks ($M_C$) can be, for example, for Carbopol 941, an estimated 104,400 g/mole. Additional polymers and drug delivery enhancing agents are described subsequently in the specification.

The present invention also relates to a pharmaceutical formulation comprising
(i) a compound of formula I and pharmaceutically acceptable salts thereof

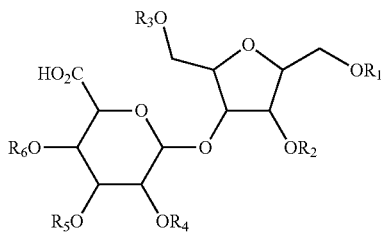

I wherein $R_1$, $R_2$, $R_4$, $R_5$ and $R_6$ are independently selected from H, $SO_3H$ or $PO_3H$ and $R_3$ is independently selected from $SO_3H$ or $PO_3H$ and
(ii) an additive selected from the group consisting of a pharmaceutically acceptable natural or synthetic polymer.

The present invention also relates to a pharmaceutical formulation comprising
(i) a compound of formula I and pharmaceutically acceptable salts thereof

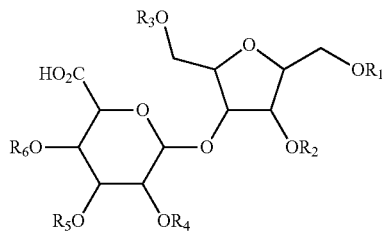

I wherein $R_1$, $R_2$, $R_5$ and $R_6$ are independently selected from H, $SO_3H$ or $PO_3H$ and $R_3$ and $R_4$ are independently selected from $SO_3H$ or $PO_3H$ and
(ii) an additive selected from the group consisting of a pharmaceutically acceptable natural or synthetic polymer.

The invention relates to a pharmaceutical formulation comprising
(i) a compound of formula I and pharmaceutically acceptable salts thereof

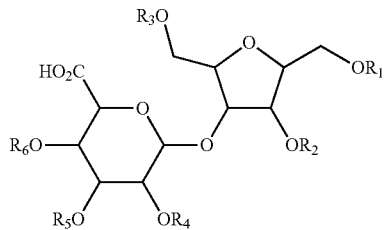

I wherein $R_1$, $R_2$ and $R_6$ are independently selected from H, $SO_3H$ or $PO_3H$ and $R_3$, $R_4$ and $R_5$ are independently selected from $SO_3H$ or $PO_3H$ and
(ii) an additive selected from the group consisting of a pharmaceutically acceptable natural or synthetic polymer.

In another embodiment, the present invention relates to a pharmaceutical formulation comprising
(i) a compound of formula II

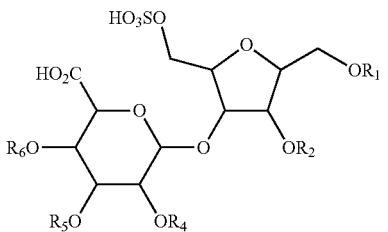

II and pharmaceutically acceptable salts thereof wherein $R_1$, $R_2$, $R_4$, $R_5$ and $R_6$ are independently selected from the group consisting of H, $SO_3H$ or $PO_3H$ and
(ii) an additive selected from the group consisting of a pharmaceutically acceptable natural or synthetic polymer.

In a preferred embodiment, the invention relates to a pharmaceutical formulation comprising
(i) a compound of formula II and pharmaceutically acceptable salts thereof

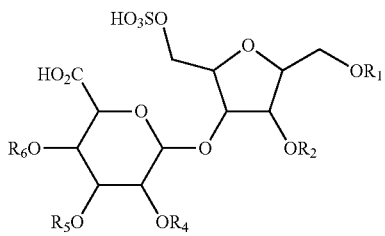

II wherein $R_1$ is $SO_3H$ and $R_2$, $R_4$, $R_5$ and $R_6$ are independently selected from H, $SO_3H$ or $PO_3H$ and
(ii) an additive selected from the group consisting of a pharmaceutically acceptable natural or synthetic polymer.

In an additional preferred embodiment, the invention relates to a pharmaceutical formulation comprising
(i) a compound of formula II and pharmaceutically acceptable salts thereof

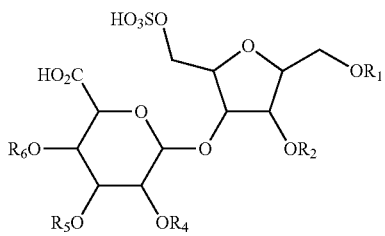

II wherein $R_1$ is $SO_3H$, $R_2$ is H and $R_4$, $R_5$ and $R_6$ are independently selected from $SO_3H$ or $PO_3H$ and
(ii) an additive selected from the group consisting of a pharmaceutically acceptable natural or synthetic polymer.

The present invention also relates to oral dosage forms comprising a compound of formula I or II and their pharmaceutically acceptable salts with $R_1$-$R_6$ as defined above and an additive selected from the group consisting of a pharmaceutically acceptable natural or synthetic polymer.

The present invention also encompasses a method of treating or alleviating an inflammatory condition comprising administration of
(i) a pharmaceutically effective amount of a formulation comprising a compound of formula I

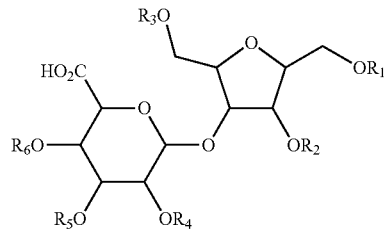

I and pharmaceutically acceptable salts thereof wherein $R_1$-$R_6$ are independently selected from $SO_3H$, $PO_3H$ or H and provided that at least two of $R_1$-$R_6$ is $SO_3H$ or $PO_3H$ and
(ii) an additive selected from the group consisting of a pharmaceutically acceptable natural or synthetic polymer.

The present invention preferably relates to a pharmaceutical formulation comprising a compound of formula I wherein $R_1$, $R_2$, $R_3$, $R_4$, $R_5$ and $R_6$ are selected from the variables shown in Table 1 as compounds 1-14 and an additive selected from the group consisting of a pharmaceutically acceptable natural or synthetic polymer.

TABLE 1

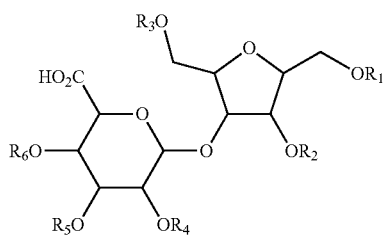

I

| Compound | $R_1$ | $R_2$ | $R_3$ | $R_4$ | $R_5$ | $R_6$ |
|---|---|---|---|---|---|---|
| 1 | —$SO_3H$ | H | —$SO_3H$ | —$SO_3H$ | H | H |
| 2 | H | —$SO_3H$ | —$SO_3H$ | —$SO_3H$ | H | H |
| 3 | H | H | —$SO_3H$ | —$SO_3H$ | H | —$SO_3H$ |
| 4 | —$SO_3H$ | H | —$SO_3H$ | —$SO_3H$ | —$SO_3H$ | H |
| 5 | —$SO_3H$ | H | —$SO_3H$ | —$SO_3H$ | H | —$SO_3H$ |
| 6 | H | H | —$SO_3H$ | —$SO_3H$ | —$SO_3H$ | —$SO_3H$ |
| 7 | —$SO_3H$ | H | —$SO_3H$ | —$SO_3H$ | —$SO_3H$ | —$SO_3H$ |
| 8 | —$SO_3H$ | —$SO_3H$ | —$SO_3H$ | —$SO_3H$ | H | H |
| 9 | H | —$SO_3H$ | —$SO_3H$ | —$SO_3H$ | —$SO_3H$ | H |
| 10 | H | —$SO_3H$ | —$SO_3H$ | —$SO_3H$ | H | —$SO_3H$ |
| 11 | —$SO_3H$ | —$SO_3H$ | —$SO_3H$ | —$SO_3H$ | —$SO_3H$ | H |
| 12 | —$SO_3H$ | —$SO_3H$ | —$SO_3H$ | —$SO_3H$ | H | —$SO_3H$ |
| 13 | H | —$SO_3H$ | —$SO_3H$ | —$SO_3H$ | —$SO_3H$ | —$SO_3H$ |
| 14 | —$SO_3H$ | —$SO_3H$ | —$SO_3H$ | —$SO_3H$ | —$SO_3H$ | —$SO_3H$ |

In a preferred embodiment, the compounds in the formulation are selected from a metal salt of a compound of formula I shown above in Table 1 wherein the carboxylic acid group is ionized and each sulfate group around the disaccharide is ionized to form a metal salt wherein the metals are selected from, for example, sodium. In addition, other salts including amine salts may form at the carboxylate or sulfate positions. The most preferred compound is compound 14 in the fully ionized form as the sodium salt (compound 14a).

The compounds of the invention may be obtained as described herein in the examples from, for example, heparin. Although the specific process used utilized porcine heparin, heparin from any mammal may be used to produce the compounds of the invention. In addition, the compounds may be derived synthetically. Various other polysaccharides may also be utilized as source materials for the recited disaccharides including, but not limited to, heparan sulfate, dermatan sulfate, chondroitin sulfate, pentosan polysulfate and other glycosaminoglycans and mucopolysaccharides.

The compounds can generally be prepared by a process which comprises (1) dissolving heparin sodium in water and adjusting the pH to be slightly acidic (about pH 6) and (2) treating this solution with sodium nitrite ($NaNO_2$) in an aqueous solution to form nitrous acid to depolymerize the heparin (and deaminate, for example, IdoA(2S)GlcNS(6S) to form IdoA(2S)-aMan) and (3) basifying the depolymerized heparin solution to a pH of about 7 and (4) diluting the depolymerized heparin solution and (5) filtering said solution to collect and enrich for heparin oligosaccharides of less than 3 kDa (3000 daltons) and (6) basifying the filtered solution containing less than 3 kDA depolymerized heparin and (7) treating this basified solution with sodium borohydride ($NaBH_4$) to reduce the aldehyde carbonyl, formed after the acidification of and depolymerization of heparin, to the alcohol; (8) treating the reduced product with concentrated acid and then adjusting the pH to about 7 and (9) further fractionating the obtained reduced oligomers using size exclusion chromatography to obtain disaccharide ammonium salts which were further treated with cation exchange resins to form the sodium salts which were further fractionated to obtain, as a major component, a compound of formula I as the sodium salt form wherein $R_1$ is H, $R_2$ is H, $R_3$ is $SO_3^-$, $R_4$ is $SO_3^-$, $R_5$ is H and $R_6$ is H and the carboxy group ($CO_2H$) is $CO_2^-Na^+$ and, as a minor component, a compound of formula I wherein $R_1$ is H, $R_2$ is H, $R_3$ is $SO_3^-$, $R_4$ is $SO_3^-$, $R_5$ is $SO_3^-$ and $R_6$ is H and the carboxy group ($CO_2H$) is $CO_2^-Na^+$ and (10) treating the resulting disaccharides with a sulfate source (e.g. $(CH_3)_3NSO_3$) under suitable conditions to form the hypersulfated disaccharides utilized in the formulations of the invention. Sulfating agents can further include $SO_3$ complexes such as $SO_3$-pyridine, $SO_3$-trimethylamine, $SO_3$-dioxan and $SO_3$-dimethylformamide and may additionally include chlorosulfonic acid, mixtures of chlorosulfonic acid and sulfuric acid and piperidine N-sulfate. The reaction is run in a suitable polar solvent such as dimethylformamide, dimethylsulfoxide or similar solvents. The temperature of the reaction can vary from room temperature to higher temperatures ranging from about 20° C. to about 70° C.

Without being limited herein, it is understood that heparin and other carbohydrates or complex carbohydrates are chiral molecules with hydroxyl groups as well as sulfate groups or carboxylic acid groups present on the ring with set or absolute stereochemistry. The most common disaccharide unit in heparin is, for example, IdoA(2S)-GlcNS(6S) which is a 2-O-sulfated iduronic acid and 6-O-sulfated glucosamine.

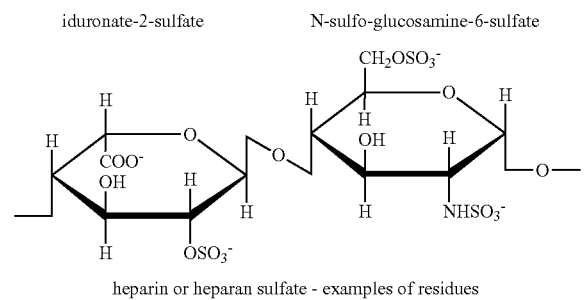

heparin or heparan sulfate - examples of residues

It is generally understood that the source of the polysaccharide which generates the oligosaccharides and disaccharides utilized in the formulations of the invention will determine, for the most part, the absolute stereochemistry of the chiral centers around the carbohydrate rings. Additional sulfate groups are added by chemical means by the process described generally above or by any known means to afford the most active moieties (hypersulfated disaccharides and salts thereof) which are further purified to form pharmaceutical grade disaccharides which are further formulated with an additive and processed into a dosage form suitable for administration to a mammal or other organism in need of treatment thereof.

Nuclear magnetic resonance imaging and/or other known structure identification methods may be used to determine the chemical structures of the molecules obtained from depolymerizing heparin (derived from any known source thereof) or other selected polysaccharide. In the event the compounds are made synthetically or semi-synthetically, the skilled artisan can use standard organic chemistry techniques to protect the desired hydroxyl moiety with a protecting group known to those of ordinary skill in the art.

A compound of formula I as described above (or mixtures thereof) is then formulated with an additive (delivery agent) to form the formulations of the invention. The additive is selected from the group consisting of any natural or synthetic polymer (as further described below) and which enhances the delivery of active ingredient into the patient or animal in need of treatment for any one of the diseases or conditions recited herein. The term "enhancing the delivery" means that there is an improvement in a quantitative or qualitative measurement of delivery of the active ingredient or active drug substance (ADS) relative to the delivery of the active ingredient that is administered without the additive (e.g. ADS+ versus ADS-). Such measurements include, but are not limited to, airway responsiveness or airway resistance as shown in the Figures presented herein. The term "pharmaceutically acceptable natural or synthetic polymer" means that the polymer is safe as administered to animals, including humans, in an administered dosage form. The additive or polymer preferably has at least one common or shared chemical and/or physical and/or biological property of the many chemical/physicali-biological properties of a polymer selected from a carbomer such as Carbopol 934P. At least one "shared property" of the polymer is preferably having side chains or groups that are ionizable. Such groups include, for example, carboxylic acid groups or other ionizable moieties such as sulfate or phosphate precursors (e.g. C—OH groups substituted with —$SO_3H$ or —$PO_3H$ size chains or variables). The relative percentage by weight on a dry basis of carboxylic acid groups or other ionizable or neutralizable groups in the polymer preferably ranges from 40-80%. Other shared properties include, but are not limited to, hydrophilicity and/or swellability and/or gelability and/or viscosity (i.e., aqueous viscosity in mPa s). Carbopol 934 P has an aqueous viscosity in a 0.5% wt/vol solution of 29,400-39,400 mPa s. Shared properties can be chemical, physical or biological. Shared biological properties include, for example, sharing the delivery properties of a Carbopol polymer across a cell membrane or tissue by transcellular means or by paracellular means through, for example, duodenal tissue or other epithelial tissue. The additive or polymer may have more than one shared property with a carbomer. The percentage of additive or agent in the formulation relative to the active ingredient can range from about 0.1% to about 80% or more on a wt/wt percentage basis. The preferred weight ratio of additive to active is 1:1 or greater (e.g. 1:1; 1.5:1; 2:1; 2.5:1; 3:1 etc).

The pharmaceutically acceptable polymer may be selected from a natural polymer such as an alginate or mixtures or alginic acid and complex salts of alginic acid which may be water soluble or water insoluble. Natural alginic acids and complexes thereof are generally described in, for example, U.S. Pat. No. 4,842,866. Alginate gums or natural polymers or gums similar to alginate gums (e.g. carrageenan gums, xanthan gums, tragacanth gums, locust bean gums, guar gums or any other complex polymers derived from plant, microbial or other natural sources and which are pharmaceutically acceptable) may be utilized in the formulation of the invention.

The pharmaceutically acceptable synthetic polymer may be selected from a hydrophobic or hydrophilic polymer. The polymer may be water soluble, slightly water soluble or water insoluble. The water soluble hydrophilic polymers may be selected from the group consisting of polyvinylpyrrolidone, hydroxypropyl cellulose, hydroxypropylmethyl cellulose, methyl cellulose, vinyl acetate/crotonic acid copolymers, methyacrylic acid polymers and copolymers, maleic anhydride/methyl vinyl ether copolymers and derivatives and mixtures thereof. The polymers may be low viscosity polymers with viscosity ranging from about 50 cps to about 200 cps and can include commercially available polymers such as Methocel™ K100 LV and similar polymers from the Dow Chemical Company. The water soluble hydrophilic polymers may also be selected from, for example, sodium carboxymethyl cellulose or other similar anionic water soluble polymers. These polymers can include polyhydroxyalkyl methacrylates, anionic or cationic hydrogels, polyvinyl alcohol or high molecular weight polyethylene oxides such as those described in various patents including, for example, U.S. Pat. No. 4,837,111.

The pharmaceutically acceptable synthetic polymer may also be selected from hydrophilic water-insoluble polymers. These are polymers that can readily absorb water, become hydrated and/or swell. These polymers can be selected from carbomers which include various Carbopol homopolymer polymers such as carboxyvinyl polymers and carboxy polymethylene or polyacrylic acid copolymers. The preferred polymers are Carbopol polymers of acrylic acid cross-linked with polyalkenyl ethers or divinyl glycol. These polymers swell and can also form gels under various conditions. The preferred Carbopol polymers include Carbopol 934P NF, Carbopol 974P NF; Carbopol 971P NF and Carbopol 71G. Other ionic polymers suitable for use in the formulation include sodium alginate, calcium carboxymethyl cellulose, sodium carboxymethyl cellulose or methyacrylic acid, acrylic acid ethyl ester copolymer. The Carbopol polymers are used in oral suspensions but are also used in dry formulations in, for example, capsules which contain or comprise a disaccharide, a Carbopol polymer and a filler such as lactose. Thus, the present invention also relates to oral suspensions or capsules or other solid dosage forms comprising a compound of formula I or II as described above and an additive selected from a polymer that swells when in contact with water or ionizes or is neutralizable or has a chemical group that facilitate the delivery or transport of the active ingredient to the site of action. The capsules or tablets may be coated with further excipients or polymers including enteric polymers. The coating materials may be selected from, for example, enteric coatings such as cellulose acetate phthalate, cellulose acetate trimelliate, hydroxypropylmethyl cellulose phthalate, copolymers of methacrylic acid and ethyl acrylate (e.g. Eudragit L30D), hydroxypropylmethyl cellulose acetate succinate or polyvinyl acetate phthalate. The preferred coatings are highly stable in the acidic environment of the stomach but break down in the more basic environment of the small intestine.

Hydrophobic polymers or additives may be selected from, for example, ethyl cellulose, polymeric methacrylic acid esters, cellulose acetate butyrate, poly(ethylele-co-vinyl-acetate), hydroxyethyl cellulose, and methacrylate polymers selected from the Eudragit polymers. Additional hydrophobic additives may be selected from waxes or fatty acid esters. It is preferred that these hydrophobic polymers swell or contain additional polymers to form blends or mixtures that swell or ionize when exposed to water or "gel". Additional "agents" that enhance the delivery of the hypersulfated disaccharides include, but are not limited to, polyanionic salts (such as polyanionic salts of glutamic acid or aspartic acid); glycosaminoglycans such as hyaluronic acid; modified amino acids; modified amino acid derivatives; alkali swellable theology modifiers; polyoxyethylene glycols; fatty acid esters; chitosan (high and low molecular weight versions as described in U.S. Pat. No. 7,291,598 and poly-glutamic acid and nanoparticles thereof; bile salts and acids thereof alone and in combination with surfactants and optional solubilizers; phospholipid polyvalent cations; phospholipase C inhibitors; unilamellar vesicles; sulphated chitinous polymers; permeabilizing reagents selected from iminodiacetic acid, nitriloacetic acid, ethylene diaminomono acetic acid, ethylene diamino diacetic acid, ethylene diamino tetraacetic acid, sodium taurodihydro fusidate, sodium caprate, sodium glycocholate, cholylsarcosine, isopropyl myristate, partially hydrolyzed triglycerides, fatty acid sugar derivatives and oleic acid derivatives; and biodegradable polymers such as poly(lactide co glycolide). Such agents are disclosed in the following publications or patents and which are herein incorporated by reference in their entirety: U.S. Pat. Nos. 5,498,410; 5,827,512; 5,908,637; 5,990,096; 6,458,383; 6,461,643; 6,635,702; 6,855,332; 7,291,598; 7,329,638; US20010024658; US20020037316; US20020115641; US20030180348; US20040038870; US20040086550; US20040096504; US20070287683 and US20090082321. These agents may be added instead of or in addition to the previously described natural or synthetic polymers.

The formulations of the invention can be delivered to the patient or other organism by any suitable known means. The percentages of the additive and type of additive added to the formulation relative to the active ingredient and other excipients will be based upon the type of formulation desired. For example, in an oral suspension formulation to be delivered to a patient or organism in need of treatment thereof, the vehicle can be an oral liquid or oral capsule. The preferred formulation is an oral capsule.

The compositions of the invention further comprise pharmaceutically acceptable excipients and/or fillers and extenders such as lactose or other sugars including but not limited to glucose, sucrose, mannitol etc. and lubricants such as magnesium stearate, talc, calcium stearate, solid polyethylene glycols, sodium lauryl sulfate and mixtures thereof. The amount of filler or lubricant or other known pharmaceutically acceptable additive will vary based upon the type of formulation and the manner the formulation is processed or made.

The compositions of the invention can be delivered or administered orally in the form of tablets, capsules or suspensions. The tablets or capsules can be prepared by means known in the art and contain a therapeutically effective amount of a hypersulfated disaccharide of formula I or II according to the invention in addition to the recited delivery agent including, for example, a polymeric additive. Tablets and pills or other suitable formulations can be prepared with enteric coatings and other release controlling coatings. Coatings can be added to afford light protection or swallowability. The capsules and tablets or suspensions can include additives which improve the taste of the medicine.

Liquid dosage forms for oral administration may include pharmaceutically acceptable emulsions, solutions, suspensions, syrups and elixers containing inert diluents such as water as well as the compounds of formula I and salts thereof and the additives selected from a pharmaceutically acceptable polymers. Such formulations may additionally include adjuvants including wetting agents, emulsifying and suspending agents, and sweetening, flavoring and perfuming agents.

The compounds of formula I and II form, as stated above, pharmaceutically acceptable salts. The metal salts include for example salts having Na, K, Ca, Ng or Ba or Al, Zn, Cu, Zr, Ti, Bi, Mn or Os or salts formed by reacting the compounds of formula I or II with an organic base such as an amino acid or with any amine. The preferred salt is a sodium salt.

Thus, the preferred formulations of the invention includes those compounds shown in Table 1 and which are sodium hypersulfated disaccharides and which further include a delivery agent selected from, for example, an additive selected from an ionic swellable hydrophilic insoluble polymer such as Carbopol 934 P. The preferred formulations are administered in the form of capsules or oral suspensions.

These formulations are useful in treating a number of inflammatory diseases and conditions. Types of respiratory diseases or conditions contemplated herein include allergic rhinitis which is characterized by seasonal or perennial sneezing, rhinorrhea, nasal congestion, and often conjunctivitis and pharyngitis; acute rhinitis, characterized by oedema of the nasal mucosa, nasal discharge and mucosa. Pulmonary diseases, such as intrinsic or extrinsic asthma bronchiale, any inflammatory lung disease, acute chronic bronchitis, pulmonary inflammatory reactions secondary to chronic bronchitis, chronic obstructive lung disease, pulmonary fibrosis, Goodpasture's syndrome as well as any lung disease or condition in which white blood cells may play a role including idiopathic pulmonary fibrosis and any other autoimmune lung disorders are treatable with the formulation of the invention.

Ear, nose and throat disorders such as acute external otitis, furunculosis and otomycosis of the external ear are treatable by the formulations of the invention. Other conditions include respiratory diseases such as traumatic and infectious myringitis, acute Eustachian salpingitis, acute serous otitis media and acute and chronic sinusitis.

Formulations of the invention are useful in treating pulmonary inflammation. The term "pulmonary inflammation" encompasses any inflammatory lung disease, acute chronic bronchitis, chronic obstructive lung disease, pulmonary fibrosis, Goodpasture's syndrome, and any pulmonary condition in which white blood cells may play a role including but not limited to idiopathic pulmonary fibrosis and any other autoimmune lung disease.

Formulations of the invention are useful in treating asthma and asthma related pathologies. The term "asthma" means a condition of allergic origin, the symptoms of which include continuous or paroxysmal labored breathing accompanied by wheezing, a sense of constriction in the chest, and, often, coughing or gasping. The term "asthma related pathologies" means a condition whose symptoms are predominantly inflammatory in nature with associated bronchospasm. Both asthma and an asthma related pathology are characterized by symptoms which include a narrowing of the airways, varying over short periods of time either spontaneously or as a result of a treatment, due in varying degrees to contraction (spasm) of smooth muscle, edema of the mucosa, and mucus in the lumen of the bronchi and bronchioles. Generally these symptoms are triggered by local release of spasmogens and vasoconstrictive substances (e.g. histamine or certain leukotrienes or prostaglandins) in the course of an allergic response. Non-limiting examples of asthma related pathologies include non-asthmatic conditions characterized by airway hyperresponsiveness (e.g. chronic bronchitis, emphysema and cystic fibrosis). The most prominent characteristic of asthma is bronchospasm, or narrowing of the airways: asthmatic patients have prominent contraction of smooth muscles of large and small airways, increased mucous production, and increased inflammation. The inflammatory response in asthma is typical for tissues covered by mucosa and is characterized by vasodilation, plasma exudation, recruitment of inflammatory cells such as neutrophils, monocytes, macrophages, lymphocytes, and eosinophils to the sites of inflammation and the release of inflammatory mediators by resident tissue cells (mast cells) or by migrating inflammatory cells (J. C. Hogg, "Pathology of Asthma," Asthma and Inflammatory Disease, P. O'Byren (ed.), Marcel Dekker, Inc., New York, N.Y. 1990, pp. 1-13).

Asthma may be triggered by multiple or a variety of causes such as in response to allergens, secondary exposure to infective agents, industrial or occupational exposures, ingestion of chemicals, exercise and/or vasculitis (Hargreave et al., J. Allergy Clinical Immunol. 83:1013-1026, 1986). As discussed herein, there may be two phases to an allergic asthma attack-an early phase and a late phase which follows 4-6 hours after bronchial stimulation (Harrison's Principles of Internal Medicine 14th Edl. Fauci et al. (eds), McGraw Hill, New York, N.Y. 1998, pp. 1419-1426). The early phase which typically resolves spontaneously, includes the immediate inflammatory response including the response caused by the release of cellular mediators from mast cells. The late phase reactions develop over a period of hours and are characterized histologically by an early influx of polymorphomuclear leukocytes and fibrin deposits followed by infiltration of eosinophils. A certain percentage of patients are "dual responders" and develop an early acute and a late phase response. In dual responders, the acute phase is followed 4-14 hours later by a secondary increase in airway resistance ("late phase response" or LPR or "late airway response" or LAR). Late responders and dual responders are of particular clinical importance because, in combination with the airway inflammation, late phase responses lead to a prolonged airway hyperreactivity (AHR), asthmatic exacerbations, or hyperresponsiveness, worsening of symptoms, and generally a more severe form of clinical asthma that may last from days to months in some subjects, requiring aggressive therapy. Pharmacological studies in allergic animals have demonstrated that not only the bronchoconstrictor response but also the inflammatory cell influx and the mediator release pattern in dual responders is quite different from acute responders.

An increase in bronchial hyperreactivity (AHR), the hallmark of a more severe form of asthma, can be induced by both antigenic and non-antigenic stimuli. Last phase response, allergen-induced asthma and persistent hyperresponsiveness have been associated with the recruitment of leukocytes, and particularly, eosinophils, to inflamed lung tissue (W. M. Abraham et al., Am. Rev. Respir. Dis. 138: 1565-1567, 1988). Eosinophils release several inflammatory mediators including 15-HETE, leukotriene C4, PAF, cationic proteins and eosinophil peroxidase.

Moreover, the formulations of the invention are also useful in treating late phase reactions and inflammatory response in extra pulmonary sites such as allergic dermatitis, inflammatory bowel disease; rheumatoid arthritis and other collagen vascular diseases, glomerulonephritis, inflammatory skin diseases and conditions; and sarcoidosis.

As used herein, the term "treating or alleviating the symptoms" means reducing, preventing and/or reversing the symptoms of the individual to which a formulation of the invention has been administered as compared to the symptoms of the individual or an individual which is untreated. Hence, a formulation of the invention that treats or alleviates the symptoms of asthma or an asthma related pathology reduces, prevents, and/or reverses the early phase asthmatic response to antigen challenge in a dual responder individual, more preferably reduces, prevents and/or reverses the late phase asthmatic response to antigen challenge in a dual responder individual, and more preferably reduces, prevents and/or reverses both the early phase and late phase responses to antigen challenge in a dual responder individual. This "treatment" or "alleviation" is preferably a significant percentage as shown in the animal models presented herein for the recited formulations and with respect to LAR and AHR data.

The terms "antigen" and "allergen" are used interchangeably to describe those substances such as dust or pollen that can induce an allergic reaction and/or induce an asthmatic episode or asthmatic symptoms in an individual suffering from such condition. Thus an individual is "challenged" when an allergen or antigen is present in a sufficient amount to trigger an asthmatic response in such individual.

It is also understood that the formulations of the invention are useful in treating any disease or condition affected by late phase reactions (LPR's). The airways are merely a prototype of organs or tissues affected by such LPR's. It has been established in the medical literature that the last phase bronchoconstriction and AHR observed in dual responder asthmatic patients is not an isolated phenomenon restricted to asthmatic or even pulmonary patients. Thus, the present formulation is useful in treating any disease or condition affected by LPR's including cutaneous, nasal, ocular and systemic manisfestations of LPR's in addition to pulmonary associated LPR's. Clinical diseases (whether of the skin, lung, nose, eye or other organs) recognized to involve allergic mechanisms have a histologic inflammatory component which follows the immediate allergic or hypersensitivity reaction that occurs on antigen challenge. This sequence of response appears to be connected to mast cell mediators and propogated by other resident cells within target organs or by cells recruited into the sites of mast cell or basophilic degranulation. Thus, the present formulation is useful in treating inflammatory bowel disease, rheumatoid arthritis, glomerulonephritis and inflammatory skin disease. The present invention therefore relates to a method of treating a patient or organism in need of treatment thereof and who/which is suffering from a disease or condition characterized by late phase allergic reactions, including e.g, and without limitation, pulmonary, nasal, cutaneous, ocular and systemic LPR's, and/or which is characterized by inflammatory reactions through the administration, by any known means, of a formulation comprising a compound of formula I or II and a delivery agent such as, for example, a polymeric additive to said patient or organism.

The term "inflammatory condition" means a disease, condition or symptom selected from the group consisting of pulmonary inflammation such as asthma and/or asthma related pathologies; pneumonia, tuberculosis, rheumatoid arthritis, allergic reactions which impact the pulmonary system, early and late phase responses in asthma and asthma related pathologies, diseases of the small and large airways of the lung, bronchospasm, inflammation, increased mucus production, conditions which involve vasodilation, plasma exudation, recruitment of inflammatory cells such as neutrophils, monocytes, macrophages, lymphocytes and eosinophils and/or release of inflammatory mediators by resident tissue cells (mast cells); conditions or symptoms which are caused by allergens, secondary responses to infections, industrial or occupational exposures, ingestion of certain chemicals or foods, drugs, exercise or vasculitis; conditions or symptoms which involve acute airway inflammation, prolonged airway hyperreactivity, increases in bronchial hyperreactivity, asthmatic exacerbations, hyperresponsiveness; conditions or symptoms which involve the release of inflammatory mediators such as 15-HETE, leukotriene C4, PAF, cationic proteins or eosinophil peroxidases; conditions or symptoms which relate to cutaneous, nasal, ocular or systemic manifestations of late phase allergic responses; clinical diseases of the skin, lung, nose, eye or throat or other organs and which involve allergic mechanisms having an histologic inflammatory component upon antigen challenge; allergic rhinitis, respiratory diseases characterized by seasonal or perennial sneezing; rhinorrhea, conjunctivitis, pharyngitis, intrinsic or extrinsic asthma bronchiale, any inflammatory lung disease, acute chronic bronchitis, pulmonary inflammatory reactions secondary to acute chronic bronchitis, chronic obstructive lung disease (COPD), pulmonary fibrosis, Goodpasture's syndrome, any pulmonary condition in which white blood cells play a role including but not limited to idiopathic pulmonary fibrosis and any other autoimmune lung disease; ear, nose and throat disorders such as acute external otitis, furunculosis and otomycosis of the external ear; respiratory diseases such as traumatic and infectious myringitis, acute eustachian salpingitis, acute serous otitis media, acute and chronic sinitis; extrapulmonary conditions selected from any late-phase reactions and inflammatory response such as allergic rhinitis; allergic dermatitis; allergic conjunctivitis; extrapulmonary diseases where inflammation occurs and/or an inflammatory response plays a major role including inflammatory bowel disease; rheumatoid arthritis and other collagen vascular diseases; glomerulonephritis; inflammatory skin diseases and sarcoidosis and cardiovascular inflammation as described below.

The present formulation may also be utilized to treat inflammatory conditions associated with cardiovascular disease. It is known that there are serious side effects associated with traditional anti-inflammatory agents such as glucocorticoid steroids and cyclophosphamide making them inappropriate choices for atherosclerotic inflammation treatment. On the other hand, the polysulfated disaccharide formulations of the invention have the advantage of having few side effects along with anti-inflammatory properties. It has clearly been postulated that atherosclerotic lesions are due to or have many properties associated with chronic inflammation including the presence of macrophages, lymphocytes and denditric cells which accumulate at specific loci to cause and/or acerbate lesions. L. K. Curtiss, N. Engl. J. Med. 360; 11 1144-1146 (2009). The present formulation is thus useful for the treatment of arteriosclerotic disorders in patients having such disorders or conditions and is further useful in the treatment or prevention of restenosis after invasive vascular surgery or after an organ transplant. The formulation suitable for cardiovascular treatment can be administered by any known means including by interal or parenteral administration. The present invention comprises a method of treating cardiovascular inflammation comprising administration of a composition comprising a compound of formula I wherein R1-R6 are as defined herein and pharmaceutically acceptable salts thereof and a delivery agent to a patient in need of treatment thereof. The present invention further includes combinations of a compound of formula I with R1-R6 as defined herein and a cardiovascular drug selected from an HMGCoA reductase inhibitor or other cardiovascular drug or drugs used to treat cardiovascular disease. The "combination" may be in the form of a single dosage form having at least two active ingredients wherein one of the active ingredients is a hypersulfated disaccharide of the invention and the other active ingredient is selected from an HMGCoA reductase inhibitor such as lovastatin, simvastatin, atorvastatin or rosavastatin calcium. In a preferred embodiment, the combination would include a formulation of the invention comprising a compound of formula I or II wherein R1-R6 is as defined herein along with a delivery agent and a second active ingredient selected from an HMGCoA reductase inhibitor.

The formulations of the invention have been found to be effective in animal studies which are predictive of utility in humans as well as other animals. The animal studies demonstrate that the formulations are useful in (a) preventing antigen-induced bronchoconstrictor response and bronchial hyperactivity (also referred to as airway-hyperresponsiveness (AHR)) and (b) in ameliorating AHR subsequent to antigen challenge in treated animals. Pulmonary airflow resistance was measured by taking allergic sheep previously verified as dual bronchoconstrictor responders to *Ascaris suum* antigen. The sheep were intubated with a cuffed nasotracheal tube and pulmonary airflow resistance (RL) was measured by the esophageal balloon catheter technique, while thoracic gas volume was measured by body plethysmography. Data were expressed as specific RL (SRL, defined as RL times thoracic gas volume (Vtg)). Airway responsiveness was determined by first securing cumulative dose response curves to inhaled carbachol (a constrictor agonist) by measuring SRL before and after inhalation of buffered saline and after each administration of 10 breaths of increasing concentrations of carbachol (0.25, 0.5, 1.0, 2.0 and 4.0% wt/vol solution). Airway responsiveness was measured by determining the cumulative provocation dose (PD400) of carbachol (in breath units) that increased SRL to 400% above baseline. One breath unit was defined as one breath of 1% carbachol solution.

As appropriate, and according to the prescribed method of administration, the formulations of the invention may be administered prior to, at the same time, or after the organism or patient has been exposed to an antigen and in relation to the particular disease or condition being treated. Doses of the active ingredient (the hypersulfated disaccharides of formula I) may range from less than 1 mg to 1,000 mgs per day. Suitable doses may also range from 0.001 mgs/kg/day to 100 mgs/kg/day or higher per treated organism. The preferred dose ranges from 0.1 mgs/kg/day to 1 mg/kg/day. One of ordinary skill in the art can modify the dose per patient or per patient groups to treat the diseases or conditions referenced herein. Capsules, tablets or suspensions may be formulated for once or twice a day administration and at doses including 5 mgs, 10 mgs, 15 mgs, 20 mgs, 25 mgs, 30 mgs, 35 mgs, 40 mgs, 45 mgs, 50 mgs, 100 mgs, and 200 mgs of active ingredient. The capsules or tablets or oral suspensions further include at least 0.1 percent (on a wt/wt basis) of delivery agent such as an additive which is selected from a polymer (natural or synthetic) or other/additional agent that enhances delivery of the active drug as recited herein.

The formulations of the invention may be administered alone or in combination with other suitable medications or active ingredients and depending upon the particular disease or condition being treated. In a preferred embodiment, the formulations or compounds of the invention are administered in the morning or evening. Thus, the present invention comprises a method of treating a disease or condition associated with antigen exposure and which involves an early and late phase response comprising administering to an organism in need thereof a therapeutically effective amount of a compound of formula I or II with R1-R6 as defined herein (i.e., with at least two sulfate groups) and a delivery enhancing agent wherein the formulation is administered in the morning or evening. The invention further comprises a method of treating a disease or condition associated with antigen exposure and which involves an early and late phase response comprising administering to an organism in need thereof a therapeutically effective amount of a compound of formula I or II with R1-R6 as defined herein and a natural or synthetic polymer or other/additional delivery enhancing agent to form a formulation and wherein said formulation is administered to the organism in the morning or evening. The additional active ingredients that may be administered in the form of combination therapy or in the form of a single dosage unit having at least two active ingredients wherein the first active is a compound of formula I or II with R1-R6 as defined herein and a second active selected from any drug or medicament which is used as front line therapy to treat asthma or an asthma related disorder or condition or other inflammatory condition as recited herein. Such medicaments include anti-inflammatories, leukotriene antagonists or modifiers, anticholinergic drugs, mast cell stabilizers, corticosteroids, immunomodulators, beta-adrenergic agonists (short acting and long acting), methyl xanthines, and other general classes or specific drugs used to treat such disorders including, but not limited to, montelukast sodium; albuterol; levoalbuterol; salmeterol; formoterol, fluticasone propionate; budesonide; ceterizine; loratadine; desloratadine; theophylline, ipratropium, cromolyn, nedocromil, beclomethasone, flunisolide, mometasone, triaminoclone, prednisoline, prednisone, zafirlukast, zileuton or omalziunab.

The following examples are intended to further illustrate certain embodiments of the invention and are non-limiting.

EXAMPLES

Example 1

Preparation of Hypersulfated Disaccharides

The compounds utilized in the formulation of the invention were prepared by initially depolyermizing heparin sodium. The starting material for preparation of the active drug substance is, for example, porcine intestinal mucosal heparin (polydisperse sulfated copolymer of 1 to 4 linked glucosamine and uronic acid residues). The active drug substance (ADS), a hypersulfated disaccharide, as described herein was shown to have anti-allergic activity in the sheep model. The production of the ADS was generally as follows:

Controlled nitrous acid depolymerization of porcine heparin;

Reduction of the end aldehyde group with NaBH4 to an alcohol;

Size exclusion chromatography (SEC) to produce the ammonium salt of the separated disaccharide;

Reaction of the disaccharide ammonium salt with sulfur trioxide pyridine complex to yield the supersulfated disaccharide;

SEC followed by cation exchange to the sodium salt afforded the final product.

The preferred product produced in this way was the hypersulfated disaccharide having six sulfate groups in the sodium salt form as shown below (compound 14a)

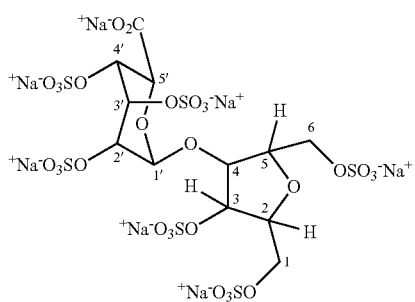

14a

Compound 14a has a solubility of >0.5 g/mL. The following procedure describes one of many possible ways to make the compounds described herein. At room temperature, 250 g of commercially available porcine heparin-Na (obtained from commercially available sources including, for example, SPL of Waunakee, Wis.) were added to a beaker containing three liters of water and stirred to a slurry, at which point two additional liters of water were added to completely dissolve the heparin salt.

The pH in the heparin solution was then adjusted to about pH 6 (5.98). To this solution was added 17.25 g of NaNO2 (0.25 mmol, J. T. Baker, ACS grade) to accomplish the controlled nitrous acid depolymerization of the heparin. Stirring was continued for 10 minutes while approximately 35.1 ml of 37% HCl was slowly added at a temperature of about 23☐ C. to bring the pH to about 3 (3.00). The temperature and pH of the solution was monitored over a two hour period (120 minutes) while the temperature went down to 20☐ C. and the pH went down to pH 2.16. The solution was then quenched by slowly adding approximately 23 ml of 50% NaOH to adjust the pH to 6.75 to afford the depolymerized heparin solution.

The depolymerized heparin solution obtained above was diluted to a final volume of 8 liters with dtH2O and filtered (Millipore (Bedford, Mass.), Pellicon 2, 3 k PLBC-C having an area of 0.5 m2 (Cassett: Cat #P2 PLBCC 05), (molecular weight cut off of 3 kDa) to collect and enrich for heparin oligosaccharides of less than 3 kDa (3000 daltons) in size (i.e., the permeate consisted of those oligosaccharides of less than 3000 daltons). The retentate that was larger than 3000 daltons was subjected to a second depolymerization treatment of nitrous acid using a 20 M solution to farther initiate the degradation of heparin. After ultrafiltration of this twice-treated oligosaccharide preparation using the same type of filter (molecular weight cut off of 3,000 daltons), the resulting permeate (with a molecular weight of less than 3 kDa) was added to the permeate from the first ultrafiltration and then the entire batch was concentrated by reverse osmosis to reduce the final volume to 2.5 liters. This was then freeze dried.

The freeze dried oligosaccharide preparation (50 g) was dissolved in 1 liter purified water and then cooled in an ice bath to 2-10☐ C. NaHCO3 (21 g) was added to the cooled oligosaccharide solution and the preparation stirred until completely dissolved. A 0.5 M solution of sodium borohydride (NaBH4) in 400 mL of 0.01 M NaOH solution was prepared and slowly added to the cooled oligosaccharide/NaHCO3 solution over a 60 minute period. The treatment of 0.5 M solution of NaBH4 was to reduce the aldehyde formed on the five membered ring (which formed after deamination) to the alcohol moiety. The reaction preparation was stirred at 2-10☐ C. for 3 hours, then quenched with concentrated HCl to pH 4.0. The pH of the solution was then adjusted to 6.75 with NaOH and finally concentrated to a minimal volume by reverse osmosis and later freeze-dried to afford the reduced oligosaccharides. The reduced oligosaccharide preparation of less than 3 kDa in size were later subjected to fractionization by size exclusion chromatography (SEC) using Bio-Rad Biogel P6 resin (elution with 0.2 M NH4HCO3) for the fractionization of the oliogmix and to collect disaccharide ammonium salts. The collected fractions were analyzed by carbazole assay, a plot of Abs530 versus fraction number afforded a profile of collected fractions. Similar fractions on profile were pooled and later lyophilized to afford the separated fractions as ammonium salts and to remove NH4HCO3. Cation exchange using Amberlite IR 120 Plus cation exchange resin (commercially available from Sigma-Aldrich) converted to ammonium salt(s) to the sodium salt form. Two disaccharides were obtained from the fractions and were identified as compounds A (85 wt %) and B (3-5 wt %):

Compound A:

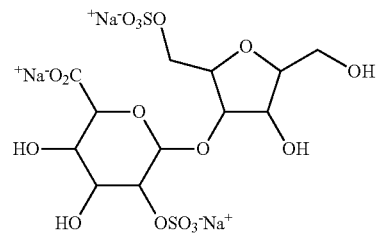

Compound B:

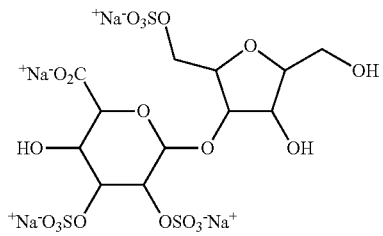

Fractions containing the above compounds A and B were further treated to form the hypersulfated disaccharides. Two non-limiting methods were utilized. In Method 1, a solution of the above fraction containing 2.5 grams disaccharide in 50 mL water was acidified through reaction with Dowex 500WX200 acidic resin commercially available from Sigma-Aldrich according to the manufacturer's instructions. The acidic filtrate was neutralized with tetrabutylammonium hydroxide and the solution was freeze-dried to obtain the tetrabutylammonium (Bu4N+) salt as a flocculent solid. Anhydrous DMF (50 mL) was then added to a mixture of the disaccharide ammonium salt and (CH3)3NSO3 (5.22 grams) under Argon. The reaction mixture was heated at 50☐ C. for 48 hours. The solution was then cooled to room temperature. 100 mls of a saturated solution of sodium acetate in ethanol was added and the mixture was stirred for twenty minutes at room temperature, diluted with 2.5 L of water and then filtered against a 500 dalton (i.e., 0.5 kDa) membrane. The retentate (i.e., larger than 0.5 kDa) was freeze-dried; resuspended in 0.2 M NH4HCO3 solution, chromatographed on Bio-Rad Biogel P6 resin (Bio-Rad, Hercules, Calif.) according to the manufacturer's instructions and eluted with 0.2 M NH4HCO3 to obtain the NH4+ salt of the hypersulfated disaccharide (3.5 grams). A portion of this salt (2.4 grams) was converted to the Na+ salt form through reaction with Amberlite IR 120 Plus cation exchange resin (commercially available from Sigma-Aldrich) according to the manufacturer's instructions to afford the sodium salt of compound 14 shown in Table I and shown below as compound 14a:

Compound 14a:

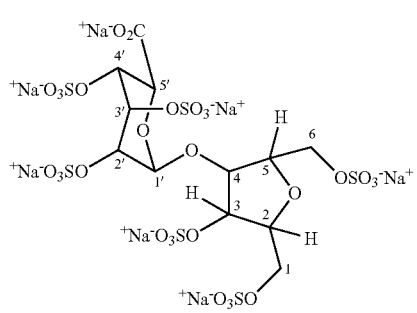

14a

This compound was also prepared according to Method 2. In Method 2, a mixture of 0.5 grams of the fraction containing compounds A and B and 3 grams of (CH3)3NSO3 in 15 mL DMF under Argon was heated at 60□ C. for 48 hours. The reaction mixture was then cooled to room temperature, diluted with 20 mL of a 10% aqueous sodium acetate solution, and stirred 20 minutes at room temperature, 100 mL of ethanol was added and the reaction mixture was concentrated under high vacuum to obtain a solid residue. The residue was dissolved in 500 mL of water and filtered against a 500 dalton membrane (washing 3× with H2O). The sodium salt retentate which contained the hypersulfated 14a product was freeze-dried to an off-white solid.

Example 2

Pulmonary Evaluation of an Animal Model (Sheep)

To illustrate the effectiveness of the formulations according to the invention to treat and alleviate allergen related diseases and conditions, including but not limited to the specific diseases and conditions recited herein, sheep were assessed in multiple experiments which compared various formulations containing no added polymer or additive to animals which were provided formulations comprising a compound of formula I (as compound 14a) along with an additive selected from a polymer. To measure pulmonary airflow resistance, the sheep were intubated with a cuffed nasotracheal tube and pulmonary airflow resistance (RL) was measured by the esophageal balloon catheter technique, while thoracic gas volume was measured by body plethysmography. These methods are accepted and well known methods found in the literature. Data were expressed as specific RL (SRL, defined as RL×thoracic gas volume (Vg).

To assess airway responsiveness, cumulative dose response curves to inhaled carbachol were performed by measuring SRL before and after inhalation of buffered saline and after each administration of 10 breaths of increasing concentrations of carbachol (0.25, 0.5, 1.0, 2.0, and 4.0% wt/vol solution). Airway responsiveness was measured by determining the cumulative provocation dose (PD400) of carbachol (in breath units) that increased SRL to 400% above baseline. One breath unit was defined as one breath of 1% carbachol solution.

For airway studies, each animal's baseline airway responsiveness (PD400) was determined and then, on different experimental days, the test sheep underwent airway challenge with *Ascaris suum* antigen. SRL was measured to establish baseline, then measured again immediately after antigen challenge and hourly for an eight hour period and then a post challenge PD400 was measured 24 hours after antigen challenge. In each of the Figures presented herein, FIGS. 1A, 2A, 3A etc. present day two data measured on an hourly basis for the eight hour period and contain control data (closed circles) and drug treatment data (open circles). The drug treatment experiments were conducted on the same animals used in the control studies but after a period of several weeks following the day 3 PD400 measurements. FIGS. 1B, 2B, 3B etc. contain the day one baseline PD400 data and day three PD400 data following antigen challenge in control or drug treated animals.

Data were expressed or may be expressed as (a) mean+/−SE % change of SRL and (b) PD400 in breath units. Data were also expressed as (c) % protection of Early Airway Response (EAR, for 0-4 hours) and Late Airway Response (LAR, for 4-8 hours), as estimated by area under the curve for EAR and LAR respectively. And (d) AHR % protection=100−Baseline PD400-drugantigen PD400×100

Baseline PD400-ControlantigenPD400

As an example, in FIG. 11B, Baseline PD400-drugantigen PD400 was 22-20.7; Baseline PD400-Controlantigen PD400 was 24−12.3, 1.3/11.7×100=10, 100−10=90% protection in AHR.

Figure 1A:
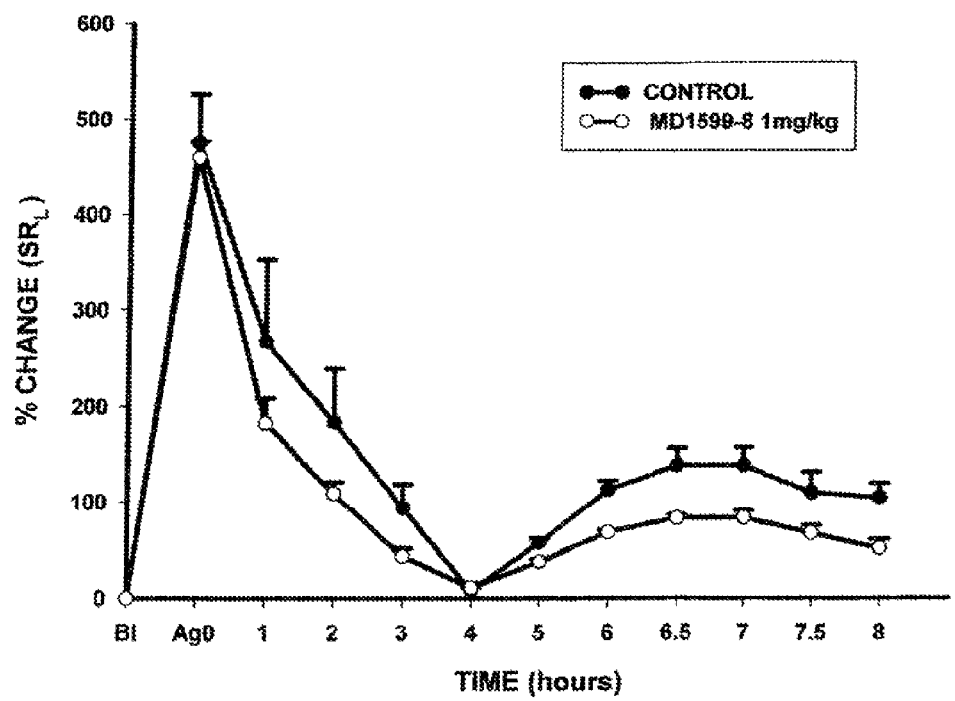
FIG. 1A shows a graph comparing the percentage change in specific pulmonary airflow resistance (measured as cm $H_2O/L/sec$) (i.e., the $SR_L$) following the indicated time after antigen administration (time=0) of sheep's responses (n=3) to exposure to antigen only (closed circles) (control) and antigen plus a liquid oral dosage of 1 mg/kg of the hexasulfated disaccharide designated as MD1599-8 or the fully ionized (at the sulfate and carboxylate positions) sodium salt form of compound 14 in Table 1 (aka compound 14a) (open circles). The MD1599-8 (compound 14a) was administered ninety minutes before antigen challenge (i.e., −1.5 hr). Data are shown as antigen-induced mean plus or minus SE % change in $SR_L$ in three sheep (n=3) exposed to antigen first with no drug and then again several weeks later with antigen plus MD1599-8 (compound 14a).
Figure 1B:
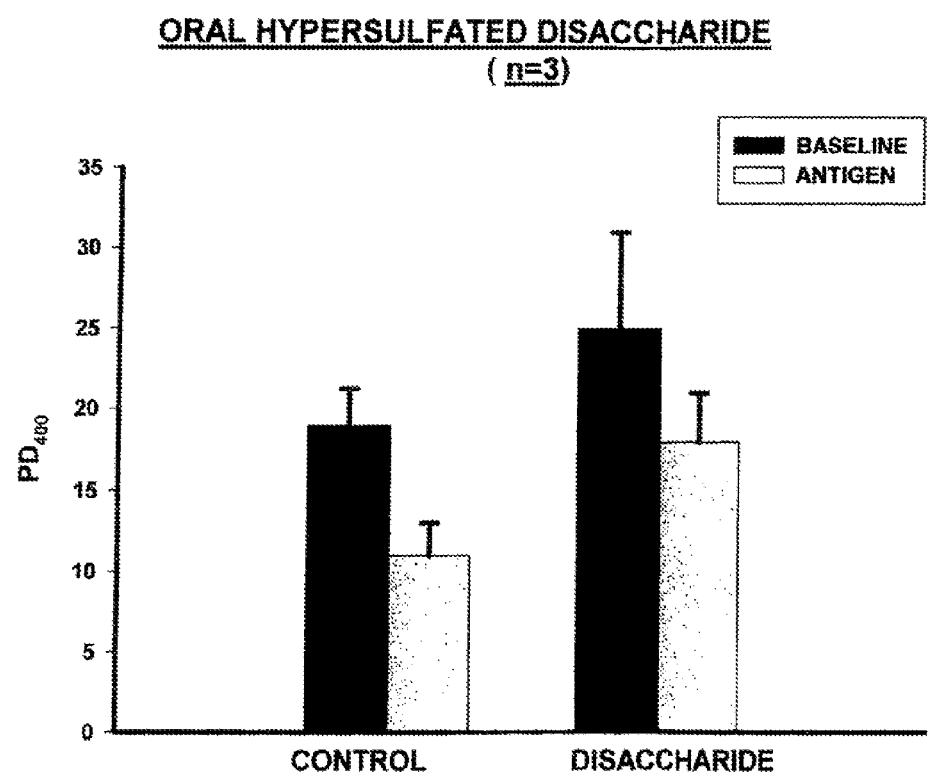
FIG. 1B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=3) exposed to antigen first with no drug and then again with antigen several weeks later following pretreatment (90 minutes beforehand) with an oral dose of MD1599-8 (Compound 14a) (1 mg/kg) in liquid form single dose. $PD_{400}$ is defined as the provocating dose of carbochol in breath units which caused a 400% increase in $SR_L$. One breath unit is one breath of 1% solution of carbochol. $PD_{400}$ is an indicator of airway responsiveness.

In the studies presented in FIGS. 1A-5B, the data shows the % change in SRL and PD400 in breath units for Control antigen response studies and for Drug-Treated antigen response studies. In the drug treated animals, liquid oral doses were given with no polymeric additive. FIG. 1A shows the % change over time in SRL in animals relative to control at an oral dosage of 1 mg/kg of compound 14a (MD1599-8). As can be seen in FIG. 1A, there is no significant effect on EAR (0-4 hr) between control and drug treatment, but there is some positive effect on LAR (4-8 hr) in the period following exposure to antigen due to drug treatment (LAR % protection=38%). As can be seen in FIG. 1B, the oral dosage of 1 mg/kg also had a slight positive effect on airway hyperresponsiveness (AHR % protection=19%).

Figure 2A:
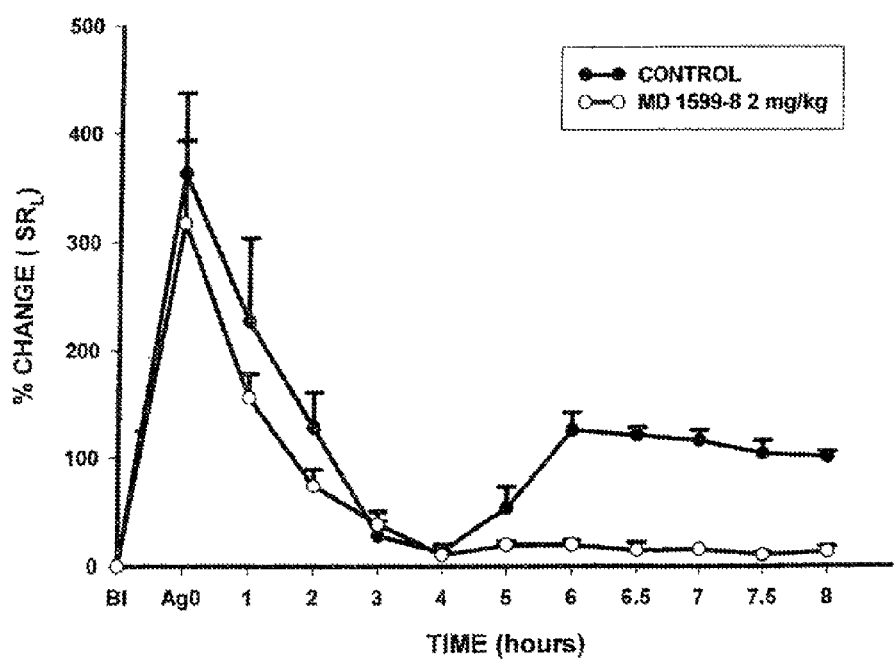
FIG. 2A shows a graph comparing the percentage change in specific pulmonary airflow resistance (i.e., the $SR_L$) following the indicated time after antigen administration (time=0) of sheep's responses (n=3) to exposure to antigen only (closed circles) (control) and antigen plus a liquid oral dosage of 2 mg/kg of the hexasulfated disaccharide designated as MD1599-8 or the fully ionized sodium salt form of compound 14 in Table 1 (compound 14a) (open circles). Data are shown as antigen-induced mean plus or minus SE % change in $SR_L$ in three sheep (n=3) exposed to antigen first with no drug and then again several weeks later with antigen plus MD1599-8. MD1599-8 was orally administered in liquid form 1.5 hours before antigen exposure.
Figure 2B:
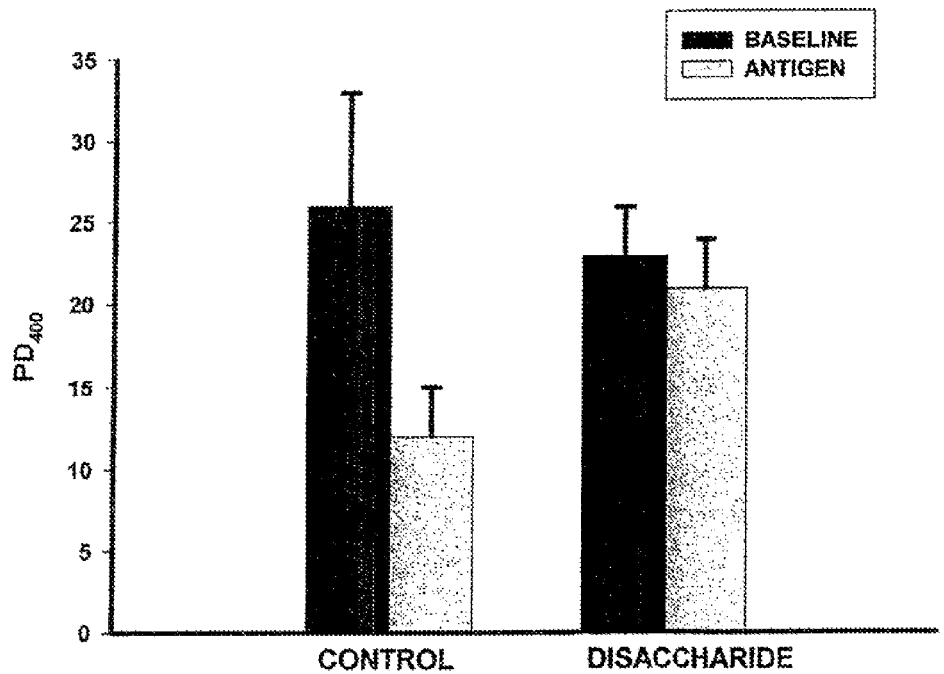
FIG. 2B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=3) exposed to antigen first with no drug and then again with antigen several weeks later following pretreatment (1.5 hours) with a liquid oral dose of MD1599-8 (2 mg/kg).

FIG. 2A shows the % change over time in SRL in animals relative to control at an oral dosage of 2 mg/kg of compound 14a (MD1599-8). As can be seen in FIG. 2A, there is some effect on EAR between control and drug treatment, but there is a more significant positive effect on LAR following exposure to antigen due to drug treatment (LAR % protection=82%). As can be seen in FIG. 2B, the oral dosage of 2 mg/kg also had a more significant positive effect on airway hyperresponsiveness (AHR % protection=85%) than the 1 mg/kg dose.

Figure 3A:
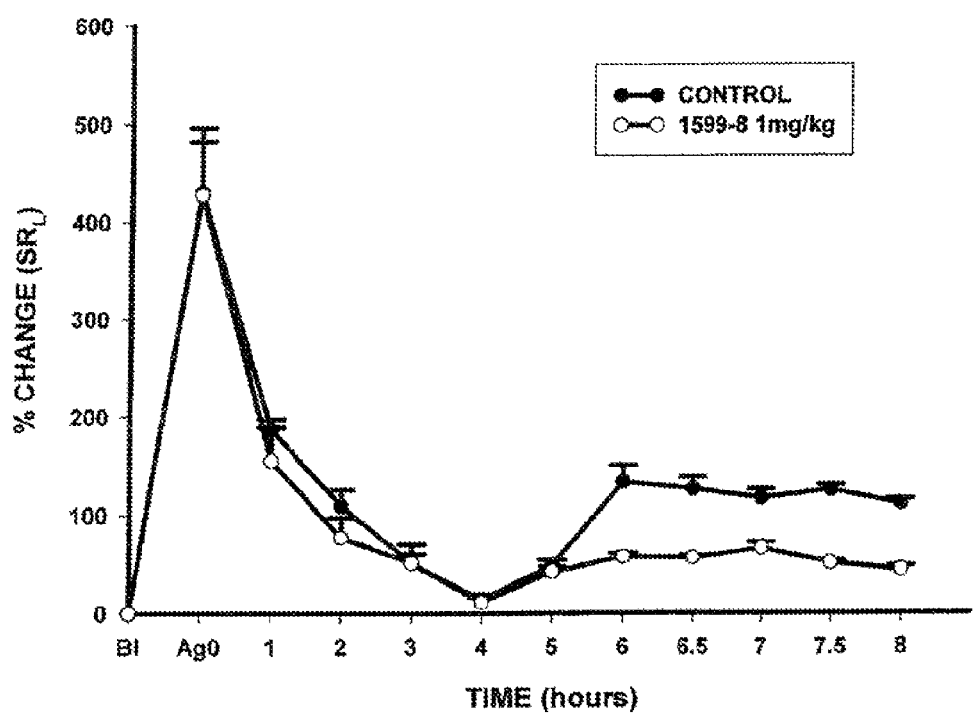
FIG. 3A shows a graph comparing the percentage change in specific pulmonary airflow resistance (measured as cm $H_2O/L/sec$) (i.e., the $SR_L$) following the indicated time after antigen administration (time=0) of sheep's responses (n=4) to exposure to antigen only (closed circles) (control) and antigen plus a liquid oral dosage of 1 mg/kg of the hexasulfated disaccharide designated as MD1599-8 or the fully ionized sodium salt form of compound 14 in Table 1 (aka compound 14a) (open circles). Data are shown as antigen-induced mean plus or minus SE % change in $SR_L$ in four sheep (n=4) exposed to antigen first with no drug and then again several weeks later with antigen after being pretreated for two days (×2 days) before antigen exposure with a total of 3 doses of 1 mg/kg MD1599-8 (compound 14a) given at 12 hour intervals in liquid form. Antigen challenge occurred 90 minutes after the last 1 mg/kg dose.
Figure 3B:
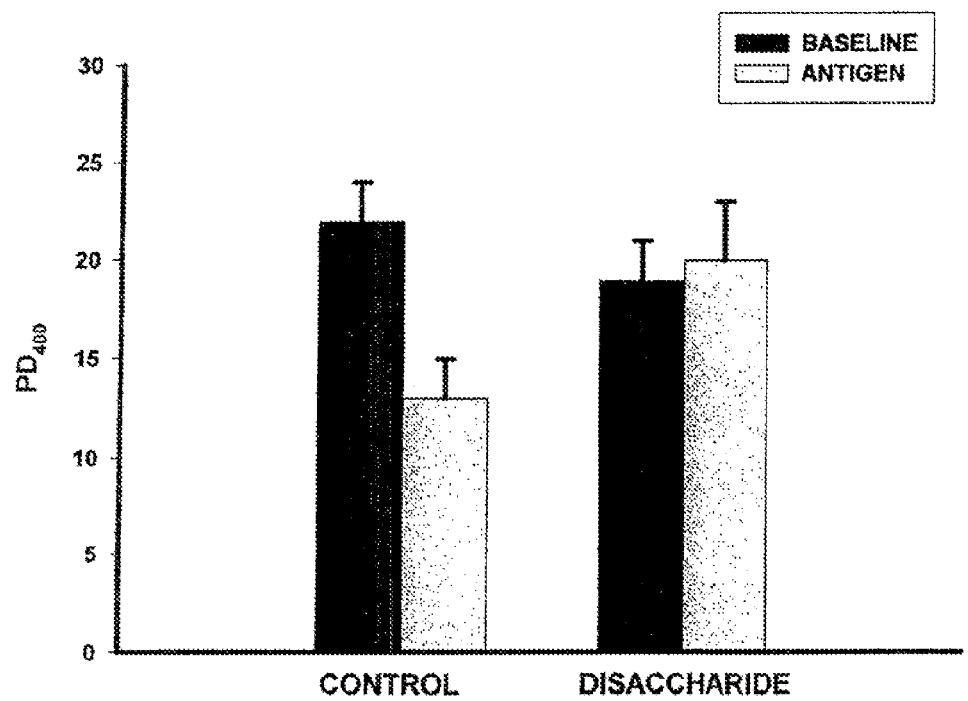
FIG. 3B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=4) exposed to antigen first with no drug and then again with antigen several weeks later following pretreatment for two days (2 days before exposure) with a liquid oral dose of MD1599-8 (compound 14a) (1 mg/kg) given 3 times at 12 hour intervals over the 2 day period. Antigen challenge occurred 90 minutes after the last 1 mg/kg dose.

FIG. 3A shows the % change over time in SRL in animals relative to control at an oral dosage of 1 mg/kg of compound 14a (MD1599-8) administered over a two day period at 12 hour intervals (3 doses of 1 mg/kg 14a). Antigen challenge occurred 90 minutes after the last 1 mg/kg dose. As can be seen in FIG. 3A, there was no effect on EAR between control and drug treatment, but there was some positive effect on LAR following exposure to antigen due to drug treatment (LAR % protection=48%). As can be seen in FIG. 3B, the oral dosage of 1 mg/kg had marked effect on airway hyperresponsiveness (AHR % protection=100%) indicating cumulative effect from drug treatment.

Figure 4A:
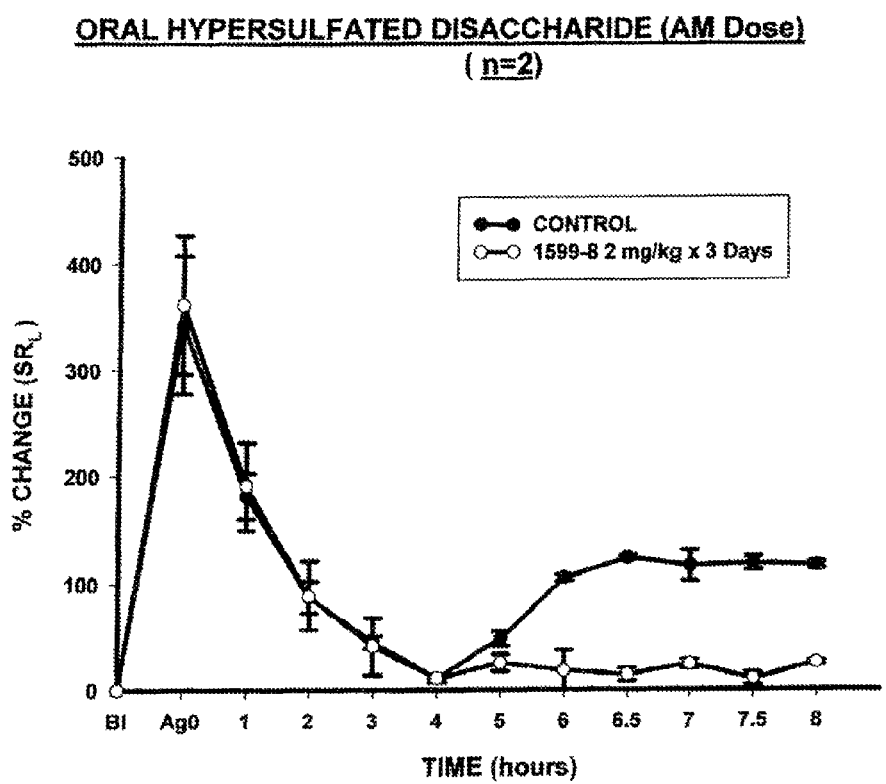
FIG. 4A shows a graph comparing the percentage change in specific pulmonary airflow resistance (measured as cm $H_2O/L/sec$) (i.e., the $SR_L$) following the indicated time after antigen administration (time=0) of sheep's responses (n=2) to exposure to antigen only (closed circles) (control) and antigen plus a liquid oral dosage of 2 mg/kg of the hexasulfated disaccharide designated as MD1599-8 or the fully ionized sodium salt form of compound 14 in Table 1 (compound 14a) (open circles). Data are shown as antigen-induced mean plus or minus SE % change in $SR_L$ in two sheep (n=2) exposed to antigen first with no drug and then again several weeks later with antigen after being pretreated for three days (×3 days) before antigen exposure with a single dose of 2 mg/kg MD1599-8 administered in the morning (A.M. dose). Antigen challenge was 24 hours after the last 2 mg/kg dose.
Figure 4B:
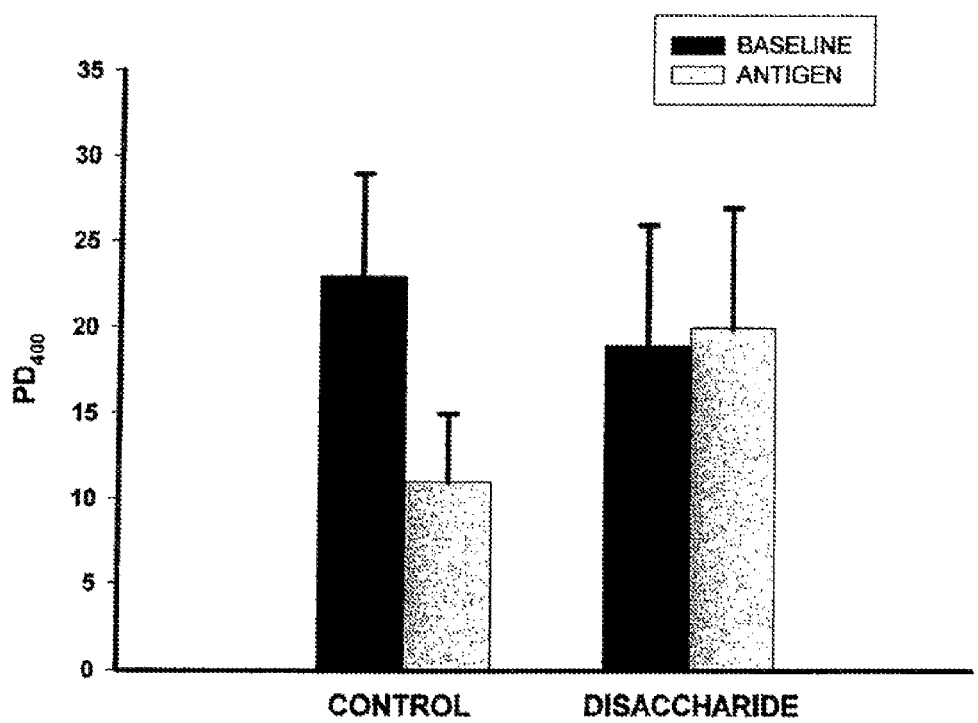
FIG. 4B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=2) exposed to antigen first with no drug and then again with antigen several weeks later following pretreatment for three days before exposure with a liquid oral dose of MD1599-8 (compound 14a) (2 mg/kg) administered in the morning for three days (2 mgs/kg/day). Antigen challenge was 24 hours after the last 2 mg/kg dose.

FIG. 4A shows the % change over time in SRL in animals relative to control at an oral dosage of 2 mg/kg of compound 14a (MD1599-8) which was administered to the sheep in the morning over a three day period. Antigen challenge occurred 24 hours after the last A.M. 2 mg/kg dose. As can be seen in FIG. 4A, there was no effect on EAR between control and drug treatment but there was a significant positive effect on LAR which was due to drug treatment (LAR % protection=78%). As can be seen in FIG. 4B, the oral dosage of 2 mg/kg administered in the above manner also had a positive effect on airway hyperresponsiveness (AHR % protection=100%).

FIG. 5A shows the % change over time in SRL in animals relative to control at an oral dosage of 2 mg/kg of compound 14a (MD1599-8) administered in the evening (P.M.) over a three day period before antigen exposure. Antigen challenge occurred 15 hours following the last 2 mg/kg evening dose. As can be seen in FIG. 5A, there is some effect on EAR between control and drug treatment and there is a significant effect on LAR following exposure to antigen due to drug treatment (LAR % protection=75%). As can be seen in FIG. 5B, the oral dosage of 2 mg/kg also had a positive effect on airway hyperresponsiveness (AHR % protection=75%).

FIGS. 6A-13B show the % change in SRL and PD400 in animals that were exposed to antigen without drug treatment and with antigen and drug formulation treatment and/or controls related thereto. Again, the A and B Figures are paired and contain control data or drug treatment data taken over a first three day period and then a second three day period after an interval of several weeks between the two treatment periods. Each of the drug formulations contain a certain dosage amount of compound 14a along with a certain weight percentage of polymer and lactose administered in an enteric coated capsule. The weight of sheep used in the studies was between 30-40 kg (avg. wt. 35 kg). Thus, for comparison purposes, a 20 mg dose given once a day is administered at an average dose of about 0.6 mg/kg/day—e.g. 20 mgs/35 kg/day.

FIG. 6A shows the % change over time in SRL in animals relative to control at an oral dosage of 15 mgs of compound 14a and 15 mgs Carbopol 934 P in a lactose filled enteric coated capsule (formulation MD1599-14) (1:1 wt/wt) administered over a three day period at night (P.M.) and with antigen challenge 15 hours following the last 15 mg dose. As can be seen in FIG. 6A, there is no effect on EAR between control and drug treatment and there is some positive effect for LAR following exposure to antigen due to drug treatment (LAR % protection=32%). As can be seen in FIG. 6B, the oral dosage of 15 mgs×3 days given at night also had a positive effect on airway hyperresponsiveness (AHR % protection=80%).

FIG. 7A shows the % change over time in SRL in animals relative to control at an oral dosage of 30 mgs of compound 14a and 30 mgs Carbopol 934 P (formulation MD1599-14) administered as two 15 mg enteric coated capsules over a three day period at night. Antigen challenge occurred 15 hours following the last 30 mg treatment. As can be seen in FIG. 7A, there is some positive effect on EAR between control and drug treatment but there is a significant positive on LAR following exposure to antigen due to drug treatment (LAR % protection=77%). As can be seen in FIG. 7B, the oral dosage of 30 mgs times 3 days at night also had a positive effect on airway hyperresponsiveness (AHR % protection=96%).

FIG. 8A shows the % change over time in SRL in animals relative to control at an oral dosage of 45 mgs of compound 14a and 45 mgs Carbopol 934 P (formulation MD1599-14) administered as three 15 mg enteric coated capsules over a three day period at night. Antigen challenge occurred 15 hours following the last 45 mg treatment. As can be seen in FIG. 8A, there is a significant positive effect on EAR between control and drug treatment and there is a significant positive effect on LAR following exposure to antigen due to drug treatment (LAR % protection=77%). As can be seen in FIG. 8B, the oral dosage of 45 mgs time 3 days at night also had a positive effect on airway hyperresponsiveness (AHR % protection=90%).

FIG. 9A shows the % change over time in SRL in animals relative to control at an oral dosage of a placebo dose of 45 mgs Carbopol 934 P and lactose filler (formulation MD1599-17) administered as three 15 mg enteric coated capsules over a three day period at night. Antigen challenge occurred 15 hours following the last 45 mg treatment. As can be seen in FIG. 19, there is no positive effect on EAR between control and placebo treatment and there is no positive effect in LAR following exposure to antigen due to placebo treatment (LAR % protection=0). As can be seen in FIG. 9B, the oral dosage of 45 mgs administered over a three day period at night also had no positive efect on airway hyperresponsiveness (AHR % protection=0).

FIG. 10A shows the % change over time in SRL in animals relative to control at an oral dosage of 21 mgs of compound 14a and 21 mgs Carbopol 934 P (formulation MD1599-19) administered as one 21 mg enteric coated capsule over a three day period at night. Antigen challenge occurred 15 hours following the last 21 mg treatment. As can be seen in FIG. 10A, there is some positive effect in EAR between control and drug treatment and there is a significant positive effect in LAR following exposure to antigen due to drug treatment (LAR % protection=78%). As can be seen in FIG. 10B, the oral dosage of 21 mgs times three days at night also had a positive effect on airway hyperresponsiveness (AHR % protection=95%).

FIG. 11A shows the % change over time in SRL in animals relative to control at an oral dosage of 21 mgs of compound 14a in lactose filler (formulation MD1599-20) administered as one 21 mg enteric coated capsule over a three day period at night. Antigen challenge occurred 15 hours following the last 21 mg treatment. As can be seen in FIG. 11A, there is no effect on EAR between control and drug treatment and there is some positive effect in LAR following exposure to antigen due to drug treatment (LAR % protection=54%). As can be seen in FIG. 11B, the oral dosage of 21 mgs also had a positive effect on airway hyperresponsiveness (AHR % protection=89%). The positive effect on LAR was unexpectedly significantly less than the 21 mg formulation having both drug and Carbopol (see FIG. 10A which had 78% protection of LAR versus 54% without Carbopol). In other words, the formulation comprising a hypersulfated disaccharide such as compound 14a and a delivery agent selected from, for example, Carbopol, provided an unexpectedly greater protection in LAR in test subjects at a non-limiting and comparative oral dosage of 0.5 mgs/kg in oral capsule (10A) form. It also provided greater protection than an oral liquid form even at a higher dose of 1 mg/kg (see FIG. 3A which showed 48% protection of LAR).

FIG. 12A also shows that two capsules of 21 mg each (42 mgs) of compound 14a without Carbopol had a positive effect on LAR (LAR % protection=76%) which was comparable to the one capsule (21 mg) having compound 14a and Carbopol (LAR % protection 78%) as shown in FIG. 10A, thus indicating that Carbopol doubled the bioavailability of the hypersulfated disaccharide versus a formulation that did not have Carbopol.

FIG. 13A shows the % change over time in SRL in animals relative to control at an oral dosage of 15 mgs of compound 14a and 30 mgs Carbopol 934 P (1:2 wt/wt ratio) (formulation MD1599-22) administered as one 15 mg enteric coated capsule over a three day period at night. Antigen challenge occurred 15 hours following the last 15 mg treatment. As can be seen in FIG. 13A, there is some positive effect on EAR between control and drug treatment and there is a significant positive effect on LAR following exposure to antigen due to drug treatment (LAR % protection=81%). This is significantly better than 32% protection of LAR seen with the 15 mg oral capsule with a 1:1 ratio of compound 14a to Carbopol (wt/wt basis) as shown in FIG. 6A. As can be seen in FIG. 13B, the oral dosage of 15 mgs compound 14a and 30 mgs Carbopol (1:2 wt/wt ratio) also had a positive effect on airway hyperresponsiveness (AHR % protection=95%). This shows that greater improvement in % protection in LAR and AHR occurs in formulations having greater ratios of polymer to drug (wt/wt basis).

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize or be able to ascertain using no more than routine experimentation, numerous embodiments of the claimed invention which may not have been expressly described. Such embodiments are within the scope of the invention.

What is claimed is:

1. A pharmaceutical formulation comprising a compound of formula I or pharmaceutically acceptable salts thereof

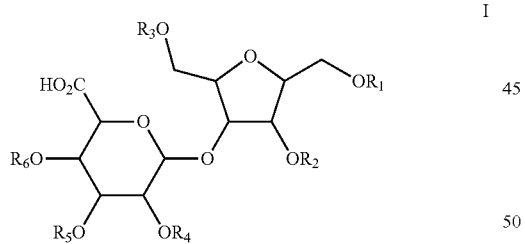

wherein $R_1$, $R_2$, $R_3$, $R_4$, $R_5$ and $R_6$ are independently selected from the group consisting of H, $SO_3H$ and $PO_3H_2$ and provided that at least two of $R_1$-$R_6$ is selected from $SO_3H$ or $PO_3H_2$ and a delivery agent selected from a natural polymer or gum or from the group consisting of polyvinylpyrollidone, hydroxypropyl cellulose, hydroxypropylmethyl cellulose, methyl cellulose, calcium carboxy methyl cellulose, vinyl acetate/crotonic acid copolymers, methacrylic acid polymers and copolymers, maleic anhydride/methyl vinyl ether copolymers and derivatives, carboxy vinyl polymer, carboxy polymethylene polymer, sodium carboxymethyl cellulose, polyhydroxyalkyl methacrylates, anionic or cationic hydrogels, polyvinyl alcohols and high molecule weight polyethylene oxides.

2. The formulation according to claim 1 wherein at least three of $R_1$-$R_6$ is selected from $SO_3H$ or $PO_3H_2$.

3. The formulation according to claim 1 wherein at least four of $R_1$-$R_6$ is selected from $SO_3H$ or $PO_3H_2$.

4. The formulation according to claim 1 wherein at least five of $R_1$-$R_6$ is selected from $SO_3H$ or $PO_3H_2$.

5. The formulation according to claim 1 wherein $R_1$-$R_6$ is selected from $SO_3H$ or $PO_3H_2$.

6. A pharmaceutical formulation comprising a compound of formula I or pharmaceutically acceptable salts thereof

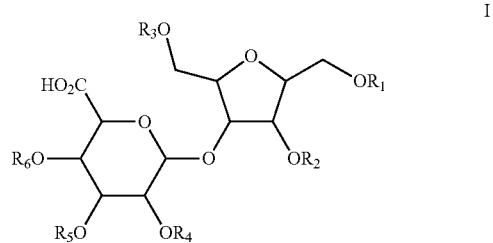

wherein $R_1$, $R_2$, $R_4$, $R_5$ and $R_6$ are independently selected from H, $SO_3H$ or $PO_3H_2$ and $R_3$ is independently selected from $SO_3H$ or $PO_3H_2$ and a delivery agent wherein the delivery agent is selected from a natural polymer or gum or from the group consisting of polyvinylpyrollidone, hydroxypropyl cellulose, hydroxypropylmethyl cellulose, methyl cellulose, calcium carboxy methyl cellulose, vinyl acetate/crotonic acid copolymers, methacrylic acid polymers and copolymers, maleic anhydride/methyl vinyl ether copolymers and derivatives, carboxy vinyl polymer, carboxy polymethylene polymer, sodium carboxymethyl cellulose, polyhydroxyalkyl methacrylates, anionic or cationic hydrogels, polyvinyl alcohols and high molecule weight polyethylene oxides.

7. A pharmaceutical formulation comprising a compound of formula I or pharmaceutically acceptable salts thereof

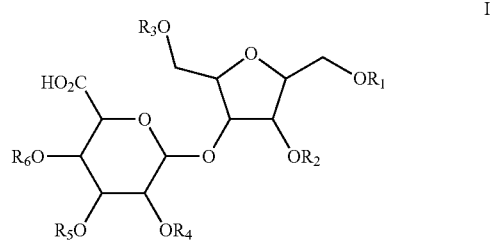

wherein $R_1$, $R_2$, $R_5$ and $R_6$ are independently selected from H, $SO_3H$ or $PO_3H_2$ and $R_3$ and $R_4$ are independently selected from $SO_3H$ or $PO_3H$ and a delivery agent selected from the group consisting of a pharmaceutically acceptable natural or synthetic polymer wherein such polymers are selected from a natural polymer or gum or from the group consisting of polyvinylpyrollidone, hydroxypropyl cellulose, hydroxypropylmethyl cellulose, methyl cellulose, calcium carboxy methyl cellulose, vinyl acetate/crotonic acid copolymers, methacrylic acid polymers and copolymers, maleic anhydride/methyl vinyl ether copolymers and derivatives, carboxy vinyl polymer, carboxy polymethylene polymer, sodium carboxymethyl cellulose, polyhydroxyalkyl methacrylates, anionic or cationic hydrogels, polyvinyl alcohols and high molecule weight polyethylene oxides.

8. A pharmaceutical formulation comprising
(i) a compound of formula I or pharmaceutically acceptable salts thereof

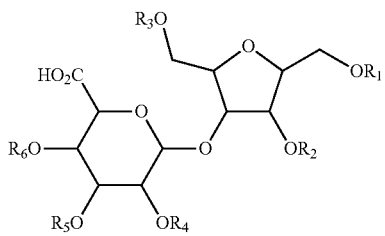

I wherein R1, R2 and R6 are independently selected from H, SO$_3$H and PO$_3$H$_2$ and R$_3$, R$_4$ and R5 are independently selected from SO$_3$H or PO$_3$H$_2$ and (ii) a delivery agent selected from a natural polymer or gum or from the group consisting of polyvinylpyrrolidone, hydroxypropyl cellulose, hydroxypropylmethyl cellulose, methyl cellulose, calcium carboxy methyl cellulose, vinyl acetate/crotonic acid copolymers, methacrylic acid polymers and copolymers, maleic anhydride/methyl vinyl ether copolymers and derivatives, carboxy vinyl polymer, carboxy polymethylene polymer, sodium carboxymethyl cellulose, polyhydroxyalkyl methacrylates, anionic or cationic hydrogels, polyvinyl alcohols and high molecule weight polyethylene oxides.

9. A pharmaceutical formulation comprising (i) a compound of formula II

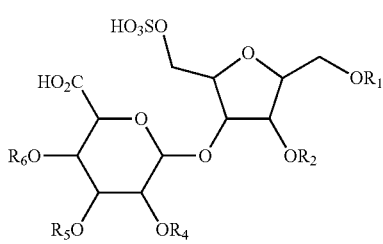

II or pharmaceutically acceptable salts thereof wherein R$_1$, R$_2$, R$_4$, R$_5$ and R$_6$ are independently selected from the group consisting of H, SO$_3$H or PO$_3$H$_2$ and (ii) a delivery agent selected from a natural polymer or gum or from the group consisting of polyvinylpyrrolidone, hydroxypropyl cellulose, hydroxypropylmethyl cellulose, methyl cellulose, calcium carboxy methyl cellulose, vinyl acetate/crotonic acid copolymers, methacrylic acid polymers and copolymers, maleic anhydride/methyl vinyl ether copolymers and derivatives, carboxy vinyl polymer, carboxy polymethylene polymer, sodium carboxymethyl cellulose, polyhydroxyalkyl methacrylates, anionic or cationic hydrogels, polyvinyl alcohols and high molecule weight polyethylene oxides.

10. A formulation comprising a compound of formula I having R$_1$-R$_6$ as

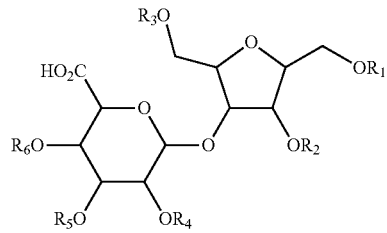

I

| R$_1$ | R$_2$ | R$_3$ | R$_4$ | R$_5$ | R$_6$ |
|---|---|---|---|---|---|
| —SO$_3$H | H | —SO$_3$H | —SO$_3$H | H | H |
| H | —SO$_3$H | —SO$_3$H | —SO$_3$H | H | H |
| H | H | —SO$_3$H | —SO$_3$H | H | —SO$_3$H |
| —SO$_3$H | H | —SO$_3$H | —SO$_3$H | —SO$_3$H | H |
| —SO$_3$H | H | —SO$_3$H | —SO$_3$H | H | —SO$_3$H |
| H | H | —SO$_3$H | —SO$_3$H | —SO$_3$H | —SO$_3$H |
| —SO$_3$H | H | —SO$_3$H | —SO$_3$H | —SO$_3$H | —SO$_3$H |
| —SO$_3$H | —SO$_3$H | —SO$_3$H | —SO$_3$H | H | H |
| H | —SO$_3$H | —SO$_3$H | —SO$_3$H | —SO$_3$H | H |
| H | —SO$_3$H | —SO$_3$H | —SO$_3$H | H | —SO$_3$H |
| —SO$_3$H | —SO$_3$H | —SO$_3$H | —SO$_3$H | —SO$_3$H | H |
| —SO$_3$H | —SO$_3$H | —SO$_3$H | —SO$_3$H | H | —SO$_3$H |
| H | —SO$_3$H | —SO$_3$H | —SO$_3$H | —SO$_3$H | —SO$_3$H |
| —SO$_3$H | —SO$_3$H | —SO$_3$H | —SO$_3$H | —SO$_3$H | —SO$_3$H | or pharmaceutically acceptable salts thereof and a delivery agent selected from a natural polymer or gum or from the group consisting of polyvinylpyrrolidone, hydroxypropyl cellulose, hydroxypropylmethyl cellulose, methyl cellulose, calcium carboxy methyl cellulose, vinyl acetate/crotonic acid copolymers, methacrylic acid polymers and copolymers, maleic anhydride/methyl vinyl ether copolymers and derivatives, carboxy vinyl polymer, carboxy polymethylene polymer, sodium carboxymethyl cellulose, polyhydroxyalkyl methacrylates, anionic or cationic hydrogels, polyvinyl alcohols and high molecule weight polyethylene oxides.

11. A method of treating or alleviating an inflammatory condition of the lung or airways in a mammal in need of treatment thereof comprising administration of
(i) a pharmaceutically effective amount of a formulation comprising a compound of formula I

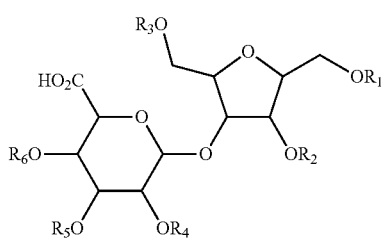

I or pharmaceutically acceptable salts thereof wherein R$_1$-R$_6$ are independently selected from SO$_3$H, PO$_3$H$_2$ or H and provided that at least two of R$_1$-R$_6$ is SO$_3$H or PO$_3$H$_2$ and (ii) a delivery agent selected from a natural polymer or gum or from the group consisting of polyvinylpyrrolidone, hydroxypropyl cellulose, hydroxypropylmethyl cellulose, methyl cellulose, calcium carboxy methyl cellulose, vinyl acetate/crotonic acid copolymers, methacrylic acid polymers and copolymers, maleic anhydride/methyl vinyl ether copolymers and derivatives, carboxy vinyl polymer, carboxy polymethylene polymer, sodium carboxymethyl cellulose, molecule polyhydroxyalkyl methacrylates, anionic or cationic hydrogels, polyvinyl alcohols and high weight polyethylene oxides.

12. The method according to claim 11 wherein the delivery agent comprises a pharmaceutically acceptable natural or synthetic polymer selected from a natural polymer or gum or from the group consisting of polyvinylpyrollidone, hydroxypropyl cellulose, hydroxypropylmethyl cellulose, methyl cellulose, calcium carboxy methyl cellulose, vinyl acetate/crotonic acid copolymers, methacrylic acid polymers and copolymers, maleic anhydride/methyl vinyl ether copolymers and derivatives, carboxy vinyl polymer, carboxy polymethylene polymer, sodium carboxymethyl cellulose, polyhydroxyalkyl methacrylates, anionic or cationic hydrogels, polyvinyl alcohols and high molecule weight polyethylene oxides.

13. The method according to claim 11 wherein at least three of $R_1$-$R_6$ is selected from $SO_3H$ or $PO_3H_2$.

14. The method according to claim 11 wherein at least four of $R_1$-$R_6$ is selected from $SO_3H$ or $PO_3H_2$.

15. The method according to claim 11 wherein at least five of $R_1$-$R_6$ is selected from $SO_3H$ or $PO_3H_2$.

16. The method according to claim 11 wherein $R_1$-$R_6$ is selected from $SO^3H$ and the delivery agent is selected from a natural polymer or gum or from the group consisting of polyvinylpyrollidone, hydroxypropyl cellulose, hydroxypropylmethyl cellulose, methyl cellulose, calcium carboxy methyl cellulose, vinyl acetate/crotonic acid copolymers, methacrylic acid polymers and copolymers, maleic anhydride/methyl vinyl ether copolymers and derivatives, carboxy vinyl polymer, carboxy polymethylene polymer, sodium carboxymethyl cellulose, polyhydroxyalkyl methacrylates, anionic or cationic hydrogels, polyvinyl alcohols and high molecule weight polyethylene oxides.

17. The method according to claim 16 wherein the polymer is selected from a natural polymer or gum.

18. The method according to claim 11 wherein the inflammatory condition is selected from pulmonary inflammation, asthma and/or asthma related pathologies; pneumonia, tuberculosis, rheumatoid arthritis, allergic reactions which impact the pulmonary system, early and late phase responses in asthma and asthma related pathologies, diseases of the small and large airways of the lung, bronchospasm, inflammation, increased mucus production, conditions which involve vasodilation, plasma exudation, recruitment of inflammatory cells such as neutrophils, monocytes, macrophages, lymphocytes and eosinophils and/or release of inflammatory mediators by resident tissue cells (mast cells); conditions or symptoms which are caused by allergens, secondary responses to infections, industrial or occupational exposures, ingestion of certain chemicals or foods, drugs, exercise or vasculitis; conditions or symptoms which involve acute airway inflammation, prolonged airway hyperreactivity, increases in bronchial hyperreactivity, asthmatic exacerbations, hyperresponsiveness; conditions or symptoms in the lungs which involve the release of inflammatory mediators such as 15-HETE, leukotriene C4, PAF, cationic proteins or eosinophil peroxidases; conditions or symptoms which relate to cutaneous, nasal, ocular or systemic manifestations of late phase allergic responses; clinical diseases of the skin, lung, nose, eye or throat or other organs and which involve allergic mechanisms having an histologic inflammatory component upon antigen challenge; allergic rhinitis, respiratory diseases characterized by seasonal or perennial sneezing; rhinorrhea, conjunctivitis, pharyngitis, intrinsic or extrinsic asthma bronchiale, any inflammatory lung disease, acute chronic bronchitis, pulmonary inflammatory reactions secondary to acute chronic bronchitis, chronic obstructive lung disease (COPD), pulmonary fibrosis, Goodpasture's syndrome, any pulmonary condition in which white blood cells play a role including but not limited to idiopathic pulmonary fibrosis and any other autoimmune lung disease; ear, nose and throat disorders such as acute external otitis, furunculosis and otomycosis of the external ear; respiratory diseases such as traumatic and infectious myringitis, acute eustachian salpingitis, acute serous otitis media, acute and chronic sinitis.

19. The method according to claim 11 wherein the mammal in need of treatment thereof is human.

20. An oral dosage form comprising
(i) a compound of formula I or a pharmaceutically acceptable salt thereof

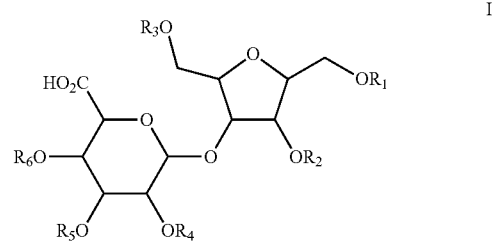

I wherein $R_1$-$R_6$ are independently selected from $SO_3H$, $PO_3H$ and H and provided that at least two of $R_1$-$R_6$ is $SO_3H$ or $PO_3H_2$ and
(ii) a delivery agent selected from a natural polymer or gum or from the group consisting of polyvinylpyrollidone, hydroxypropyl cellulose, hydroxypropylmethyl cellulose, methyl cellulose, calcium carboxy methyl cellulose, vinyl acetate/crotonic acid copolymers, methacrylic acid polymers and copolymers, maleic anhydride/methyl vinyl ether copolymers and derivatives, carboxy vinyl polymer, carboxy polymethylene polymer, sodium carboxymethyl cellulose, polyhydroxyalkyl methacrylates, anionic or cationic hydrogels, polyvinyl alcohols and high molecule weight polyethylene oxides.

* * * * *